United States Patent
Kitagawa et al.

(10) Patent No.: US 9,753,187 B2
(45) Date of Patent: Sep. 5, 2017

(54) LOW HYDROUS SOFT OPHTHALMIC LENS AND METHOD FOR MANUFACTURING THE SAME

(75) Inventors: Rumiko Kitagawa, Otsu (JP); Masataka Nakamura, Otsu (JP); Satoru Ogasahara, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 101 days.

(21) Appl. No.: 14/239,071

(22) PCT Filed: Aug. 15, 2012

(86) PCT No.: PCT/JP2012/070775
§ 371 (c)(1),
(2), (4) Date: Jun. 6, 2014

(87) PCT Pub. No.: WO2013/024880
PCT Pub. Date: Feb. 21, 2013

(65) Prior Publication Data
US 2014/0333893 A1    Nov. 13, 2014

(30) Foreign Application Priority Data

Aug. 17, 2011  (JP) .................................. 2011-178665
Mar. 1, 2012   (JP) .................................. 2012-045096

(51) Int. Cl.
*A61L 31/06* (2006.01)
*A61F 2/14* (2006.01)
(Continued)

(52) U.S. Cl.
CPC ................ *G02B 1/043* (2013.01); *A61F 2/14* (2013.01); *A61F 2/1613* (2013.01); *A61L 27/18* (2013.01);
(Continued)

(58) Field of Classification Search
CPC ... G02B 1/043; G02B 1/12; A61F 2/14; A61F 2002/009; A61F 2/16; A61F 2/1613;
(Continued)

(56) References Cited

U.S. PATENT DOCUMENTS 4,153,641 A    5/1979   Deichert et al.
4,189,546 A    2/1980   Deichert et al.
(Continued)

FOREIGN PATENT DOCUMENTS

CN    1186550       7/1998
CN    1327002 A    12/2001
(Continued)

OTHER PUBLICATIONS

Chinese Office Action to Corresponding Chinese Application No. CPCH1363712P, CN20120039912.9, dated May 29, 2015.
(Continued)

*Primary Examiner* — Thomas K Pham
*Assistant Examiner* — Ibrahima Diedhiou
(74) *Attorney, Agent, or Firm* — RatnerPrestia

(57) ABSTRACT

Provided are a low hydrous soft ophthalmic lens that can remarkably reduce or avoid a phenomenon in which a lens sticks to a cornea when worn and can reduce a decrease in the performance of a coating layer when rubbing the low hydrous soft ophthalmic lens for cleaning and a method for manufacturing the same. The low hydrous soft ophthalmic lens has a layer formed of a hydrophilic polymer on at least part of the surface of a base material containing a polysiloxane compound, and at least part of the inside of the layer is cross-linked.

8 Claims, 1 Drawing Sheet

(51) Int. Cl.

| | | |
|---|---|---|
| *A61F 2/16* | (2006.01) | |
| *B29D 11/00* | (2006.01) | |
| *C08L 33/02* | (2006.01) | |
| *C08L 33/26* | (2006.01) | |
| *G02B 1/04* | (2006.01) | |
| *G02B 1/12* | (2006.01) | |
| *A61L 27/18* | (2006.01) | |
| *A61L 27/50* | (2006.01) | |
| *C08L 79/02* | (2006.01) | |

(52) U.S. Cl.
CPC ............... *A61L 27/50* (2013.01); *A61L 31/06* (2013.01); *B29D 11/00009* (2013.01); *B29D 11/00038* (2013.01); *B29D 11/00865* (2013.01); *C08L 33/02* (2013.01); *C08L 33/26* (2013.01); *C08L 79/02* (2013.01); *G02B 1/12* (2013.01); *A61L 2430/16* (2013.01); *C08L 2205/03* (2013.01)

(58) Field of Classification Search
CPC .......... A61L 27/16; A61L 27/18; A61L 27/34; A61L 27/50; A61L 27/52; A61L 31/10; A61L 2430/16; A61L 2400/18; A61K 31/727; A61K 31/728; A61K 31/79; B05D 3/068; B05D 7/02; B29D 11/00038; B29D 11/00865; C08L 33/02; C08L 33/14; C08L 33/26; C08L 39/06; C08L 51/06; C08L 51/08; C08L 79/02; C08L 83/04; C08L 101/14; C08L 2205/03; C08F 220/34; C08J 7/18; Y10T 428/31507; Y10T 428/31794; Y10T 428/31663
USPC .......... 351/159.3, 159.02; 264/1.1; 427/2.24, 427/496; 428/412, 421, 447, 482; 522/167, 84, 85; 623/6.57
See application file for complete search history.

(56) References Cited

U.S. PATENT DOCUMENTS

| | | |
|---|---|---|
| 4,208,506 A | 6/1980 | Deichert et al. |
| 4,277,595 A | 7/1981 | Deichert et al. |
| 4,543,398 A | 9/1985 | Bany et al. |
| 4,806,382 A | 2/1989 | Goldberg et al. |
| 4,954,586 A | 9/1990 | Toyoshima et al. |
| 5,302,678 A * | 4/1994 | Nomura ............... C08F 220/28 351/159.33 |
| 5,807,944 A | 9/1998 | Hirt |
| 6,043,328 A | 3/2000 | Domschke |
| 8,124,668 B2 | 2/2012 | Baba et al. |
| 2002/0006521 A1 | 1/2002 | Shimoyama et al. |
| 2002/0016383 A1* | 2/2002 | Iwata ............... B29D 11/00125 351/159.04 |
| 2006/0142410 A1 | 6/2006 | Baba et al. |
| 2006/0251694 A1 | 11/2006 | Nielsen et al. |
| 2012/0314183 A1 | 12/2012 | Nakamura et al. |

FOREIGN PATENT DOCUMENTS

| | | |
|---|---|---|
| CN | 1723411 A | 1/2006 |
| CN | 1742042 A | 3/2006 |
| JP | 54-24047 | 2/1979 |
| JP | 54-081363 | 6/1979 |
| JP | 56-51715 | 5/1981 |
| JP | 59-229524 | 12/1984 |
| JP | 02-188717 | 7/1990 |
| JP | 05-005861 | 1/1993 |
| JP | 2000-010055 | 1/2000 |
| JP | 2002-501211 | 1/2002 |
| JP | 2002-047365 | 2/2002 |
| JP | 2005-309228 | 11/2005 |
| JP | 2005-538418 | 12/2005 |
| JP | 2006-201263 | 8/2006 |
| JP | 2008-122937 | 5/2008 |
| JP | 2009-540369 | 11/2009 |
| JP | 5954170 B2 | 7/2016 |
| TW | 419487 | 1/2001 |
| WO | WO 99/35520 | 7/1999 |
| WO | WO 2004/025332 | 3/2004 |
| WO | WO 2004/063795 | 7/2004 |
| WO | WO 2007/146137 | 12/2007 |
| WO | WO 2011/102356 | 8/2011 |

OTHER PUBLICATIONS

International Search Report for PCT Application No. PCT/JP2012/070775 dated Oct. 30, 2012.
European Search Report for EP 12824340.9 dated May 11, 2015.
Chinese Office Action dated Sep. 24, 2014, application No. 201280039912.9.
Chinese Office Action dated Dec. 2, 2015 in Chinese Application No. 201280039912.9.
Japanese Office Action for Japanese Application No. 101129840, dated Mar. 17, 2016.
Japanese Office Action with English language translation for Application No. 2012-545970, dated Feb. 23, 2017, 3 pages.

* cited by examiner

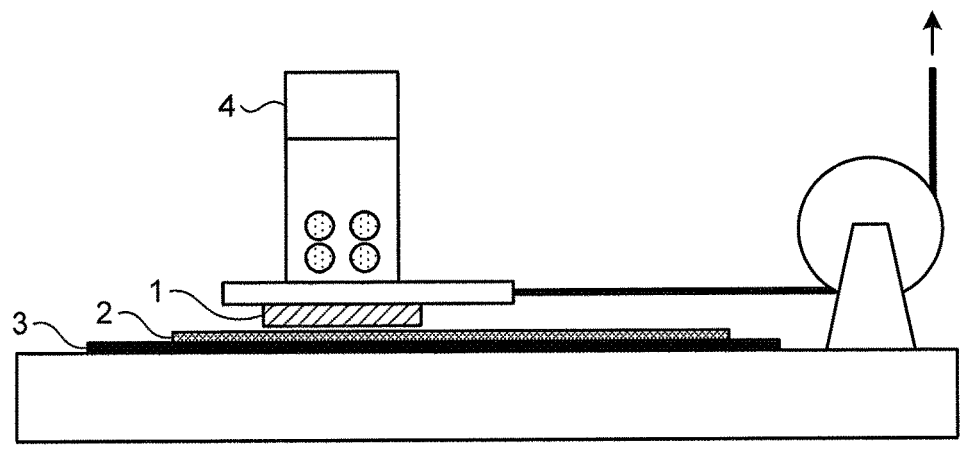

LOW HYDROUS SOFT OPHTHALMIC LENS AND METHOD FOR MANUFACTURING THE SAME

CROSS REFERENCE TO RELATED APPLICATION

This application is the U.S. National Phase application of PCT International Application No. PCT/JP2012/070775, filed Aug. 15, 2012, and claims priority to Japanese Patent Application No. 2011-178665, filed Aug. 17, 2011, and Japanese Patent Application No. 2012-045096, filed Mar. 1, 2012, the disclosure of each are incorporated herein by reference in their entireties for all purposes.

FIELD OF INVENTION

The present invention relates to a low hydrous soft ophthalmic lens and a method for manufacturing the same.

BACKGROUND OF THE INVENTION

Soft contact lenses are a representative example of commercial soft ophthalmic lenses. A hydrogel material having a water content of about 25% to about 80% is generally used for commercial soft contact lenses. However, because a hydrous soft contact lens formed of the hydrogel material contains water, a phenomenon in which water vaporizes from the contact lens occurs. This caused a certain percentage of contact lens wearers to have a stronger dry feeling than with the naked eyes and feel uncomfortable. Some complained of a symptom called contact lens dry eye. The hydrous soft contact lens formed of the hydrogel material is likely to be contaminated with some components within lacrimal fluid, and has a risk of growth of bacteria because it contains a large amount of water.

A known example of highly oxygen permeable low hydrous soft contact lenses is a silicone rubber lens obtained by a method including adding a platinum catalyst to a mixture of polydimethylsiloxane with both ends of its molecular chain capped with vinyl methyl silyl groups and methyl hydrogen polysiloxane and heat curing the mixture by molding (see Patent Literature 1).

Described in Patent Literatures 2 to 6 and the like are contact lens materials having high oxygen permeability mainly consisting of polysiloxane having a plurality of polymerizable functional groups. Among them, disclosed in Patent Literature 6 is a contact lens material formed of a polymer obtained from a bifunctional organic siloxane macromer alone or obtained by copolymerizing the macromer with another monomer. Disclosed monomers for use in the copolymerization are acrylic acid fluoroalkyl esters or methacrylic acid fluoroalkyl esters and acrylic acid alkyl esters or methacrylic acid alkyl esters.

However, the conventional highly oxygen permeable low hydrous soft contact lenses have the following problems. First, the silicone rubber lens has failed to achieve wide practical use owing to drawbacks including the peeling off of a hydrophilization-treated layer formed in order to improve the hydrophobicity of the lens surface and the occurrence of adhesion onto a cornea resulting from its too much elasticity.

The material mainly consisting of polysiloxane having a plurality of polymerizable functional groups is, having high oxygen permeability and also flexibility, considered as one of the materials suitable for contact lenses. However, adhesiveness remains on the lens surface after polymerization, which may cause adhesion of the lens to a cornea, and is unsatisfactory in the balance of flexibility and mechanical properties such as resistance to bending as a lens.

Various methods are known for modifying the surface of soft ophthalmic lenses, and known among them is a method including applying layers of two or more kinds of polymer materials one layer after another and stacking them (e.g., see Patent Literatures 7 to 9). Among them, a method that applies polymer materials having opposite electric charges alternately one layer after another is called the LbL method or the like, in which it is considered that the layers of one material are noncovalently bonded to the other layers of the different material. However, the highly oxygen permeable soft ophthalmic lens that clearly demonstrates the usefulness of that method is only those having a silicone hydrogel material, and the usefulness with respect to the low hydrous soft ophthalmic lenses has not been known. Conventional LbL coating has been performed with multiple layers including about 4 to 20 layers, which might make a manufacturing process longer and cause an increase in manufacturing costs.

With respect to another method for modifying the surface of ophthalmic lenses, Patent Literature 10 discloses irradiating a lens with a specific ethylene oxide derivative brought into contact therewith with radiation to fix the ethylene oxide derivative onto the lens surface. Patent Literature 11 discloses immersing an ophthalmic lens into a solution of a hydrophilic compound containing a water-soluble peroxide and gives rise to graft copolymerization. Patent Literature 12 discloses immersing a hydrogel base material into a solution of a macromolecular compound and irradiating the hydrogel base material with gamma rays.

However, none of these pieces of Patent Literature 10 to 12 discloses surface treatment for reducing or avoiding a phenomenon of sticking of the lens to a cornea when worn.

Patent Literature 13 discloses a method for manufacturing a soft ophthalmic lens in which a layer formed of an acidic polymer and a basic polymer (hereinafter, a coating layer) is formed on at least part of the surface of a base material for a soft ophthalmic lens, thereby remarkably reducing or avoiding a phenomenon of sticking of the lens to a cornea when worn and achieving to manufacture the lens by a simple process and economically.

However, for two-week wearing or one-month wearing disposable ophthalmic lenses, the performance of the coating layer may decrease when worn or when rubbing the ophthalmic lens for cleaning, the method needs improvement.

PATENT LITERATURE

Patent Literature 1: Japanese Laid-open Patent Publication No. 54-81363
Patent Literature 2: Japanese Laid-open Patent Publication No. 54-24047
Patent Literature 3: Japanese Laid-open Patent Publication No. 56-51715
Patent Literature 4: Japanese Laid-open Patent Publication No. 59-229524
Patent Literature 5: Japanese Laid-open Patent Publication No. 02-188717
Patent Literature 6: Japanese Laid-open Patent Publication No. 05-5861
Patent Literature 7: Japanese National Publication of International Patent Application No. 2002
Patent Literature 8: Japanese National Publication of International Patent Application No. 2005-538418

Patent Literature 9: Japanese National Publication of International Patent Application No. 2009-540369

Patent Literature 10: Japanese Laid-open Patent Publication No. 2005-309228

Patent Literature 11: Japanese Laid-open Patent Publication No. 2000-10055

Patent Literature 12: Japanese Laid-open Patent Publication No. 2008-122937

Patent Literature 13: WO 2011/102356

SUMMARY OF THE INVENTION

The present invention has been achieved in view of the above circumstances, and an object thereof is to provide a low hydrous soft ophthalmic lens that can remarkably reduce or avoid a phenomenon in which a lens sticks to a cornea when worn and can reduce a decrease in the performance of a coating layer when rubbed for cleaning and a method for manufacturing the same. Another object of the present invention is to manufacture such a low hydrous soft ophthalmic lens by a simple process and economically.

In order to solve the above problems and achieve the objects, the present invention has the following aspects.

A low hydrous soft ophthalmic lens according to the present invention includes: a base material; and a layer formed of a hydrophilic polymer on at least part of a surface of the base material, at least part of inside of the layer being cross-linked.

Moreover, a low hydrous soft ophthalmic lens according to the present invention includes: a lens-shaped silicon-containing base material; and a layer formed of a hydrophilic polymer on at least part of a surface of the silicon-containing base material by applying a coating onto the silicon-containing base material, wherein the hydrophilic polymer contains a nitrogen atom and no silicon atom, and $Y-X \geq 0.05$ and $Z-X \geq 0.04$ are satisfied, where X is a N/Si element content ratio that is the ratio of a nitrogen atom content with respect to a silicon atom content on a lens surface before the coating, Y is the N/Si element content ratio on the lens surface after the coating and before rubbing for cleaning, and Z is the N/Si element content ratio on the lens surface after rubbing for cleaning.

The above X has the same meaning as "a N/Si element content ratio that is the ratio of a nitrogen atom content with respect to a silicon atom content on part of the base material on which no coating is applied."

Moreover, a low hydrous soft ophthalmic lens according to the present invention includes: a lens-shaped silicon-containing base material; and a layer formed of a hydrophilic polymer on at least part of a surface of the silicon-containing base material, wherein the hydrophilic polymer contains a nitrogen atom and no silicon atom, and $Y-Z \leq 0.05$ is satisfied, where Y is a N/Si element content ratio that is the ratio of a nitrogen atom content with respect to a silicon atom content on a lens surface before rubbing for cleaning, and Z is the N/Si element content ratio on the lens surface after rubbing for cleaning.

In the above-described low hydrous soft ophthalmic lens, it is preferable that the hydrophilic polymer is an acidic polymer and/or basic polymer.

In the above-described low hydrous soft ophthalmic lens, it is preferable that the base material and the layer cross-link therebetween at least partially.

In the above-described low hydrous soft ophthalmic lens, it is preferable that part of the inside of the layer is cross-linked by irradiating the base material with radiation while the acidic polymer and/or basic polymer is/are attached to the base material.

In the above-described low hydrous soft ophthalmic lens, the base material has, as a main component, a polymer of a component A below or a copolymer of the component A below and a component B below: the component A is a polysiloxane compound having a plurality of polymerizable functional groups per molecule and a number average molecular weight of 6,000 or more; and the component B is a polymerizable monomer having a fluoroalkyl group.

In the above-described low hydrous soft ophthalmic lens, it is preferable that the layer is formed by performing treatment with an acidic polymer solution once or twice and treatment with a basic polymer solution once or twice, these pieces of treatment being performed three times in total.

In the above-described low hydrous soft ophthalmic lens, it is preferable that the layer is formed by performing treatment with two kinds of acidic polymer solutions twice and treatment with a basic polymer solution once.

In the above-described low hydrous soft ophthalmic lens, it is preferable that at least one kind of hydrophilic polymer forming the layer is a polymer having a group selected from a hydroxy group and an amido group.

A method for manufacturing a low hydrous soft ophthalmic lens according to the present invention includes the steps 1 to 4 in this order:

step 1 of polymerizing a mixture of monomers to obtain a lens-shaped molded body;

step 2 of bringing the molded body into contact with a basic polymer solution and rinsing off an excess basic polymer solution;

step 3 of bringing the molded body into contact with an acidic polymer solution and rinsing off an excess acidic polymer solution; and step 4 of irradiating the molded body with radiation.

A method for manufacturing a low hydrous soft ophthalmic lens according to the present invention includes the step of forming, on a lens-shaped silicon-containing base material, a layer formed of an acidic polymer and a basic polymer onto at least part of a surface of the silicon-containing base material by coating, wherein at least one of the basic polymer and the acidic polymer contains a nitrogen atom and no silicon atom, and $Y-X \geq 0.05$ and $Z-X \geq 0.04$ are satisfied, where X is a N/Si element content ratio that is the ratio of a nitrogen atom content with respect to a silicon atom content on a lens surface before the coating, Y is the N/Si element content ratio on the lens surface after the coating and before rubbing for cleaning, and Z is the N/Si element content ratio on the lens surface after rubbing for cleaning.

A method for manufacturing a low hydrous soft ophthalmic lens according to the present invention includes the step of forming, on a lens-shaped silicon-containing base material, a layer formed of an acidic polymer and a basic polymer onto at least part of a surface of the lens-shaped silicon-containing base material by coating. It is preferable that at least one of the basic polymer and the acidic polymer contains a nitrogen atom and no silicon atom and that $Y-Z \leq 0.05$ is satisfied, where Y is a N/Si element content ratio that is the ratio of a nitrogen atom content with respect to a silicon atom content on the lens surface after the coating, and Z is the N/Si element content ratio on the lens surface after rubbing for cleaning.

In the above-described method for manufacturing a low hydrous soft ophthalmic lens, it is preferable that the mixture of monomers is a mixture containing a component A that is a polysiloxane compound having a plurality of polymerizable functional groups per molecule and a number average molecular weight of 6,000 or more and a component B that is a polymerizable monomer having a fluoroalkyl group.

In the above-described method for manufacturing a low hydrous soft ophthalmic lens, it is preferable that the step of irradiating the layer with radiation is further included after the step of coating.

In the above-described method for manufacturing a low hydrous soft ophthalmic lens, it is preferable that the dose of the radiation is 1 kGy or more and 40 kGy or less.

In the above-described method for manufacturing a low hydrous soft ophthalmic lens, it is preferable that the radiation is gamma rays or electron rays.

In the above-described method for manufacturing a low hydrous soft ophthalmic lens, it is preferable that the radiation is gamma rays with a dose of 1 kGy or more and 25 kGy or less or electron rays with a dose of 1 kGy or more and 40 kGy or less.

The low hydrous soft ophthalmic lens according to the present invention can remarkably reduce or avoid a phenomenon of sticking to a cornea when worn, which has been regarded as a problem in conventional low hydrous soft ophthalmic lenses. The low hydrous soft ophthalmic lens according to the present invention can reduce the risk of the growth of bacteria, because of being low hydrous. A preferable aspect of the present invention can provide a low hydrous soft ophthalmic lens that has high oxygen permeability, excellent wettability, flexibility and an excellent wearing feeling, and further excellent mechanical properties such as resistance to bending. The low hydrous soft ophthalmic lens according to the present invention also has the advantage of capable of being manufactured by a simple process and economically. The low hydrous soft ophthalmic lens according to the present invention has the advantage of improving the durability of a coating layer, because a layer formed of a hydrophilic polymer is formed on at least part of the surface, and at least part of the inside of the layer is cross-linked.

BRIEF DESCRIPTION OF THE DRAWING

FIG. 1 is a schematic diagram of an apparatus for measuring a dynamic friction force between a sample film and synthetic leather.

DETAILED DESCRIPTION OF EMBODIMENTS OF THE INVENTION

Described below are embodiments of a low hydrous soft ophthalmic lens and a method for manufacturing the same according to the present invention. It should be noted that the present invention is not limited to the embodiments.

In the low hydrous soft ophthalmic lens according to the present invention, the low hydrous means that the water content is 10% by mass or less. The soft means that the tensile modulus of elasticity is 10 MPa or less.

The water content here is, for example, given, using the mass of a test piece in the shape of a contact lens under dry condition and mass when wiping off moisture on the surface of the test piece under wet condition owing to a borate buffered solution (mass under wet condition), by [{(the mass under wet condition)−(the mass under dry condition)}/the mass under wet condition] (% by mass).

In the present specification, the wet condition means a condition in which a sample has been immersed into pure water or a borate buffer solution at room temperature (23° C. to 25° C.) for 24 hours or more. The measurement of physical property values under the wet condition is performed as promptly as possible after the sample is taken out of the pure water or the borate buffer solution.

In the present specification, the dry condition means a condition in which a sample under the wet condition has been vacuum dried at 40° C. for 16 hours. The degree of vacuum in the vacuum drying is 2 hPa or less. The measurement of physical property values under the dry condition is performed as promptly as possible after the vacuum drying.

The borate buffer solution in the present specification is a "saline solution" described in Example 1 of Japanese National Publication of International Patent Application No. 2004-517163. Specifically, 8.48 g of sodium chloride, 9.26 g of boric acid, 1.0 g of sodium borate (sodium tetraborate decahydrate), and 0.10 g of ethylenediaminetetraacetic acid are dissolved in pure water to prepare a 1,000 mL of an aqueous solution.

Because of being low hydrous, the low hydrous soft ophthalmic lens according to the present invention has the characteristic of providing a smaller dry feeling in the eyes of a wearer and wearing comfort. Because of being low hydrous, the low hydrous soft ophthalmic lens according to the present invention has the advantage of being low in the risk of the growth of bacteria. The water content is more preferably 5% by mass or less, further preferably 2% by mass or less, and most preferably 1% by mass or less. A too high water content is unfavorable, because a dry feeling in the eyes of a wearer of the ophthalmic lens becomes higher or the risk of the growth of bacteria increases.

The lower limit of the tensile modulus of elasticity of the low hydrous soft ophthalmic lens according to the present invention is preferably 0.01 MPa or more and more preferably 0.1 MPa or more. The upper limit of the tensile modulus of elasticity of the low hydrous soft ophthalmic lens according to the present invention is preferably 5 MPa or less, more preferably 3 MPa or less, further preferably 2 MPa or less, still further preferably 1 MPa or less, and most preferably 0.6 MPa or less. When the tensile modulus of elasticity is too low, handling tends to become difficult, because of being too soft. When the tensile modulus of elasticity is too high, a wearing feeling tends to become worse, because of being too hard. A tensile modulus of elasticity of 2 MPa or less is preferable, because a favorable wearing feeling is obtained, and a tensile modulus of elasticity of 1 MPa or less is preferable, because a more favorable wearing feeling is obtained. The tensile modulus of elasticity is measured for a sample under the wet condition owing to a borate buffer solution.

The tensile elongation (elongation at break) of the low hydrous soft ophthalmic lens according to the present invention is preferably 100% to 1,000% and more preferably 200% to 700%. Low tensile elongation is unfavorable, because the low hydrous soft ophthalmic lens becomes likely to be broken. Too high tensile elongation is unfavorable, because the low hydrous soft ophthalmic lens tends to be likely to become deformed. The tensile elongation is measured for a sample under the wet condition owing to a borate buffer solution.

The ophthalmic lens has a dynamic contact angle (when advancing, immersion speed: 0.1 mm/sec) of preferably 100° or less, more preferably 90° or less, and further preferably 80° or less. In view of preventing sticking to the cornea of a wearer, the dynamic contact angle is preferably lower; it is preferably 65° or less, more preferably 60° or less, further preferably 55° or less, still further preferably 50° or less, and most preferably 45° or less. The dynamic contact angle is measured for a sample under the wet condition owing to a borate buffer solution with respect to a borate buffer solution.

In view of preventing sticking to the cornea of a wearer, liquid film retaining time of the surface of the ophthalmic lens is preferably longer. The liquid film retaining time here is a time period during which, when the ophthalmic lens immersed in a borate buffer solution is pulled up out of the liquid and held in the air so that its diameter direction is vertically directed, a liquid film on the surface of the ophthalmic lens is held without being drained. The liquid film retaining time is preferably 5 seconds or more, more preferably 10 seconds or more, and most preferably 20 seconds or more. The diameter here is the diameter of a circle formed by the perimeter of the ophthalmic lens.

In view of preventing sticking to the cornea of a wearer, the surface of the ophthalmic lens preferably has excellent slidability. As an indicator indicating slidability, friction measured by a method described in the examples of the present specification is preferably lower. The friction is preferably 60 gf (0.59 N) or less, more preferably 50 gf (0.49 N) or less, further preferably 40 gf (0.39 N) or less, and most preferably 30 gf (0.29 N) or less. Because extremely low friction tends to make it difficult to handle it when putting on and off, the friction is 5 gf (0.049 N) or more and preferably 10 gf (0.098 N) or more. The friction is measured for a sample under the wet condition owing to a borate buffer solution.

The antifouling property of the ophthalmic lens can be evaluated by mucin adhesion, lipid (methyl palmitate) adhesion, and an artificial lacrimal fluid immersion test. A smaller adhesion amount by these pieces of evaluation is preferable, because it gives an excellent wearing feeling and a reduced risk of the growth of bacteria. The mucin adhesion amount is preferably 5 µg/cm$^2$ or less, more preferably 4 µg/cm$^2$ or less, and most preferably 3 µg/cm$^2$ or less.

In view of oxygen supply from an atmosphere to the eyes of an ophthalmic lens wearer, the low hydrous soft ophthalmic lens preferably has high oxygen permeability. The oxygen permeability coefficient [×10$^{-11}$(cm$^2$/sec)mLO$_2$/(mL·hPa)] is preferably 50 to 2,000, more preferably 100 to 1500, further preferably 200 to 1,000, and most preferably 300 to 700. Too much increased oxygen permeability is unfavorable, because other properties such as mechanical properties may be affected. The oxygen permeability is measured for a sample under the dry condition.

The low hydrous soft ophthalmic lens according to the present invention is a low hydrous soft ophthalmic lens including a lens-shaped molded body (hereinafter, called a base material), and a layer formed of a hydrophilic polymer is formed on at least part of the surface of the base material, and at least part of the inside of the layer is cross-linked. The hydrophilic polymer is, for example, an acidic polymer and/or a basic polymer.

In order to have high oxygen permeability and obtain strong adhesiveness with a polymer to be applied on its surface without covalent bonding, the base material preferably contains silicon atoms in an amount of 5% by mass or more. The base material containing silicon atoms in an amount of 5% by mass or more will be called a silicon-containing base material below.

The silicon atom content (% by mass) is calculated based on the mass of the base material under the dry condition (100% by mass). The silicon atom content of the base material is preferably 5% by mass to 36% by mass, more preferably 7% by mass to 30% by mass, further preferably 10% by mass to 30% by mass, and most preferably 12% by mass to 26% by mass. A too high silicon atom content is unfavorable, because the tensile modulus of elasticity may increase.

The silicon atom content of the base material can be measured by the following method. A sufficiently dried base material is put into a platinum crucible in a metered manner and is, with sulfuric acid added thereto, heated and ashed by a hot plate and a burner. The ash is fused with sodium carbonate and is, with water added thereto, heated and melted. After that, nitric acid is added thereto, and the volume is fixed with water. For this solution, silicon atoms are measured by the ICP spectrometry to determine the content within the base material.

The base material preferably has as a main component a polymer of a component A that has a plurality of polymerizable functional groups per molecule and is a polysiloxane compound with a number average molecular weight of 6,000 or more or a copolymer of the component A and a compound that has a polymerizable functional group and is different from the component A. The main component here means a component contained in an amount of 50% by mass or more based on the mass of the base material under the dry condition (100% by mass). The polysiloxane compound here is a compound having a bond represented by Si—O—Si—O—Si.

In the present invention, the hydrophilic polymer is a polymer that satisfies either of the following conditions:

(1) A polymer that dissolves in water in a concentration of 0.01% by mass or more at 25° C. It may be heated during the dissolving process.

(2) A polymer whose, when a coating layer is formed, water content of the coating layer is 10% by mass or more at 25° C., based on the dry mass of the coating layer. The water content here is a value with the mass of water attached to the surface excluded.

Because the silicon-containing base material contains silicon, carbon, oxygen atoms and the like, elementary analysis on the surface of the base material detects elements such as Si, C, and O. The hydrophilic polymer such as an acidic polymer and a base polymer for use in the formation of the coating layer in the present invention is an organic compound, and at least one polymer among the polymers contains nitrogen atoms and does not any silicon atom. When using a polymer whose nitrogen element content is higher than the nitrogen element content of the silicon-containing base material, the nitrogen atom content per unit area increases after applying coating. In this case, the adhesion amount of the coating layer can be evaluated with an increase in the nitrogen atom content.

Elementary analysis on the base material or the lens surface after coating can be performed using the X-ray photoelectron spectroscopy (hereinafter, abbreviated as XPS). XPS irradiates the surface of a sample with X-rays and measures the energy of photoelectrons generated thereby, thereby analyzing constituent elements of the sample and their electronic states. More specifically, when the sample is irradiated with X-rays, the X-rays enter an area with a depth of a few micrometers from the sample surface, and only when the depth from the sample surface is in a range of about a few nanometers to a few tens of nanometers, photoelectrons can escape. As a result, only photoelectrons generated in the very vicinity of the surface are detected. Using this phenomenon, the nanometer-order chemical state of the lens surface can be analyzed. An excitation X-ray is preferably Al or Mg, and Al is used in the present invention. The photoelectron take-off angle (the inclination of a detector with respect to the sample surface) is set to be 90°.

The XPS analysis can obtain the ratio of a specific element content with respect to an all-element content detected. Because, as described above, data in the area of a depth of a few nanometers from the lens surface is obtained, a silicon content after coating generally detected is less than a silicon content before coating.

In view of the above, when purely comparing increases in the layer of a hydrophilic polymer by coating using an increase in nitrogen, with a nitrogen element content (%) and a silicon element content (%) obtained by XPS being R(N) and R(Si), respectively, a parameter R(N)/R(Si) (=the nitrogen element content/the silicon element content) is useful. Hereinafter, this parameter will be called a N/Si element content ratio.

With a N/Si element content ratio before coating being X and a N/Si element content ratio after coating being Y, the difference between Y and X (Y−X) is an indicator of the adhesion amount of the hydrophilic polymer as a coating layer. Y−X is preferably 0.05 or more, more preferably 0.07 or more, and most preferably 0.08 or more.

Because the N/Si element content ratio before coating (X) cannot be directly measured from the lens after coating, a value measured as follows can be used as a substitute. Specifically, first, the lens after coating is divided into two with a sharp and clean knife to expose a section of the lens. This section of the lens is shaped in a bow form. Next, the measurement of the N/Si element content ratio is performed at a position in the vicinity of the top of the bow shape of the section and in the vicinity of the center of the section in the thickness direction, thereby determining X.

In view of actual use conditions of the lens, with the N/Si element content ratio after performing predetermined rubbing for cleaning on the lens after coating under the conditions described below being Z, Z−X is an indicator of resistance to rubbing for cleaning. Z−X is preferably 0.04 or more, more preferably 0.05 or more, and most preferably 0.06 or more.

In view of actual use conditions of the lens, after the coating, the difference between the N/Si element content ratio before rubbing for cleaning (Y) and a N/Si element content ratio after rubbing for cleaning (Z) (Y−Z) is preferably 0.05 or less, more preferably 0.04 or less, further preferably 0.03 or less, and particularly preferably 0.02 or less.

The boundary values indicating the respective preferable ranges of the above Y−X, Z−X, and Y−Z are values obtained by measuring X, Y, and Z to the third decimal place and rounding off Y−X, Z−X, and Y−Z calculated using X, Y, and Z to the second decimal place.

The silicon atom content (% by mass) in the present invention is calculated based on the mass of the base material under the dry condition (100% by mass). The lower limit of the silicon element content is, as described above, preferably 5% by mass or more, more preferably 7% by mass or more, further preferably 10% by mass or more, and most preferably 12% by mass or more. The upper limit thereof is preferably 36% by mass or less, more preferably 30% by mass or less, and most preferably 26% by mass or less. A too high content of silicon atom is unfavorable, because the tensile modulus of elasticity may increase.

The silicon-containing base material preferably has as a main component a polymer of a component A that has a plurality of polymerizable functional groups per molecule and is a polysiloxane compound or a copolymer of the component A and a compound that has a polymerizable functional group and is different from the component A.

The compound different from the component A is preferably any combination of:

Component B: a polymerizable monomer having a fluoroalkyl group;

Compound M: a monofunctional monomer having one polymerizable functional group per molecule and a siloxanyl group; and Compound C: a component different from the component A, the component B, and the component M.

The main component means a component contained in an amount of 50% by mass or more based on the mass of the base material under dry condition (100% by mass).

The number average molecular weight of the component A is preferably 6,000 or more. The inventors have found that the number average molecular weight of the component A being in this range gives a low hydrous soft ophthalmic lens that has flexibility and an excellent wearing feeling and further has excellent mechanical properties such as resistance to bending. Because of being capable of obtaining a low hydrous soft ophthalmic lens that has more excellent mechanical properties such as resistance to bending, the number average molecular weight of the component A is preferably 8,000 or more. The number average molecular weight of the component A is preferably in a range of 8,000 to 100,000, more preferably in a range of 9,000 to 70,000, and further preferably in a range of 10,000 to 50,000. A too low number average molecular weight of the component A is unfavorable, because mechanical properties such as resistance to bending tend to decrease, and in particular, when it is less than 6,000, resistance to bending decreases. A too high number average molecular weight of the component A is unfavorable, because flexibility and transparency tend to decrease.

Because the low hydrous soft ophthalmic lens according to the present invention is an optical product, its transparency is preferably high. As a criterion of transparency, it is preferably transparent and free from cloudiness under visual observation. When being observed by a lens projector, it is preferable for the ophthalmic lens that almost no cloudiness is observed, and it is the most preferable that no cloudiness is observed.

The degree of dispersion (a value obtained by dividing the mass average molecular weight by the number average molecular weight) of the component A is preferably 6 or less, more preferably 3 or less, further preferably 2 or less, and most preferably 1.5 or less. When the degree of dispersion of the component A is low, the following advantages arise: compatibility with other components increases; the transparency of a lens obtained increases; an extractable component contained in a lens obtained decreases; and a shrinkage rate involved in lens molding reduces. The shrinkage rate involved in lens molding can be evaluated by a lens molding ratio=[a lens diameter]/[the diameter of a cavity of a mold]. The diameter here is the diameter of a circle formed by the perimeter of a lens. As the lens molding ratio becomes close to 1, it becomes easy to manufacture high-quality lenses stably. The molding ratio is preferably in a range of 0.85 to 2.0, more preferably in a range of 0.9 to 1.5, and most preferably 0.91 to 1.3.

In the present invention, the number average molecular weight of the component A is a number average molecular weight in terms of polystyrene measured by the gel permeation chromatography method (the GPC method) with chloroform used as a solvent. The mass average molecular weight and the degree of dispersion (a value obtained by dividing the mass average molecular weight by the number average molecular weight) are also measured by a similar method. For the other components, the number average molecular weight, the mass average molecular weight, and the degree of dispersion are measured by a similar method.

The present specification may express the mass average molecule weight as Mw and the number average molecular weight as Mn. A molecular weight of 1,000 may be expressed as 1 kD. For example, the expression "Mw33 kD" expresses "a mass average molecular weight of 33,000."

The component A is a polysiloxane compound having a plurality of polymerizable functional groups. The number of the polymerizable functional groups of the component A may be two or more per molecule, and in view of being likely to obtain a more flexible (low-modulus) ophthalmic lens, the number is preferably two per molecule. A particularly preferable structure has the polymerizable functional groups at both ends of a molecular chain.

The polymerizable functional group of the component A is preferably a radical polymerizable functional group and more preferably one having a carbon-carbon double bond. Preferable examples of the polymerizable functional group include a vinyl group, an allyl group, a (meth)acryloyl group, α-alkoxymethyl acryloyl group, a maleic acid residue, a fumaric acid residue, an itaconic acid residue, a crotonic acid residue, a isocrotonic acid residue, and a citraconic acid residue. Among these, because of having higher polymerizability, a (meth)acryloyl group is the most preferable.

In the present specification, the term (meth)acryloyl expresses both methacryloyl and acryloyl. The same holds for the terms (meth)acryl, (meth)acrylate, and the like.

The component A preferably has a structure of Formula (A1) below:

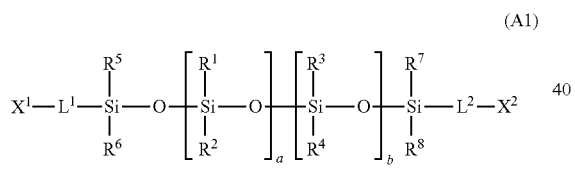

(A1)

In Formula (A1), $X^1$ and $X^2$ each independently represent a polymerizable functional group. $R^1$ to $R^8$ each independently represent a substituent selected from a hydrogen atom, a $C_1$ to $C_{20}$ alkyl group, a phenyl group, and a $C_1$ to $C_{20}$ fluoroalkyl group. $L^1$ and $L^2$ each independently represent a divalent group. The symbols a and b each independently represent the number of respective repeating units.

$X^1$ and $X^2$ are preferably a radical polymerizable functional group and are preferably one having a carbon-carbon double bond. Preferable examples of the polymerizable functional group include a vinyl group, an allyl group, a (meth)acryloyl group, α-alkoxymethyl acryloyl group, a maleic acid residue, a fumaric acid residue, an itaconic acid residue, a crotonic acid residue, a isocrotonic acid residue, and a citraconic acid residue. Among these, because of having higher polymerizability, a (meth)acryloyl group is the most preferable.

Preferable examples of $R^1$ to $R^8$ include: a hydrogen atom; a $C_1$ to $C_{20}$ alkyl group such as a methyl group, en ethyl group, a propyl group, an isopropyl group, a butyl group, a t-butyl group, a decyl group, a dodecyl group, and octadecyl group; a phenyl group; and a $C_1$ to $C_{20}$ fluoroalkyl group such as a trifluoromethyl group, a trifluoroethyl group, a trifluoropropyl group, a tetrafluoropropyl group, a hexafluoroisopropyl group, a pentafluorobutyl group, a heptafluoropentyl group, a nonafluorohexyl group, a hexafluorobutyl group, a heptafluorobutyl group, an octafluoropentyl group, a nonafluoropentyl group, a dodecafluoroheptyl group, a tridecafluoroheptyl group, a dodecafluorooctyl group, a tridecafluorooctyl group, a hexadecafluorodecyl group, a heptadecafluorodecyl group, a pentafluoropropyl group, a tetradecafluorooctyl group, a pentadecafluorooctyl group, an octadecafluorodecyl group, and a nonadecafluorodecyl group. Among these, in view of imparting favorable mechanical properties and high oxygen permeability to an ophthalmic lens, a hydrogen atom and a methyl group are more preferable, and a methyl group is the most preferable.

$L^1$ and $L^2$ are preferably a $C_1$ to $C_{20}$ divalent group. Among these, because of having the advantage of being likely to obtain the compound (A1) in high purity, $L^1$ and $L^2$ are preferably groups represented by Formulae (LE1) to (LE12) below. Among these, groups represented by Formulae (LE1), (LE3), (LE9), and (L11) below are more preferable, groups represented by Formulae (LE1) and (LE3) below are further preferable, and a group represented by Formula (LE1) below is the most preferable. Formulae (LE1) to (LE12) below are represented with the left side as an end bonded to the polymerizable functional group $X^1$ or $X^2$ and with the right side as an end bonded to a silicon atom.

 (LE1)

 (LE2)

 (LE3)

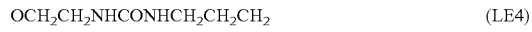 (LE4)

 (LE5)

 (LE6)

 (LE7)

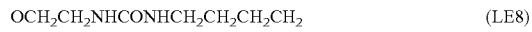 (LE8)

 (LE9)

 (LE10)

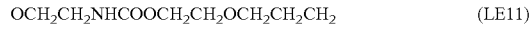 (LE11)

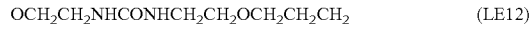 (LE12)

In Formula (A1), a and b each independently represent the number of respective repeating units. The symbols a and b are each independently preferably within a range of 0 to 1,500. The sum of a and b (a+b) is preferably 80 or more, more preferably 100 or more, more preferably 100 to 1,400, more preferably 120 to 950, and further preferably 130 to 700.

When $R^1$ to $R^8$ are all a methyl group, b=0, and a is preferably 80 to 1,500, more preferably 100 to 1400, more preferably 120 to 950, and further preferably 130 to 700. In this case, the value of a is determined by the molecular weight of the polysiloxane compound of the component A.

Only one type of the component A according to the present invention may be used, or two or more types thereof may be used in combination.

As the other compound to be compolymerized with the component A, the above-described component B that is a polymerizable monomer having a fluoroalkyl group has water repellent and oil repellent properties owing to a decrease in critical surface tension caused by the fluoroalkyl group, thereby producing the effect of preventing the surface of an ophthalmic lens from being contaminated by components in lacrimal fluid such as protein and lipid. The component B also produces the effect of providing a low hydrous soft ophthalmic lens that has flexibility and an excellent wearing feeling and further has excellent mechanical properties such as resistance to bending. Specific preferable examples of the fluoroalkyl group of the component B include a $C_1$ to $C_{20}$ fluoroalkyl group such as a trifluoromethyl group, a trifluoroethyl group, a trifluoropropyl group, a tetrafluoropropyl group, a hexafluoroisopropyl group, a pentafluorobutyl group, a heptafluoropentyl group, a nonafluorohexyl group, a hexafluorobutyl group, a heptafluorobutyl group, an octafluoropentyl group, a nonafluoropentyl group, a dodecafluoroheptyl group, a tridecafluoroheptyl group, a dodecafluorooctyl group, a tridecafluorooctyl group, a hexadecafluorodecyl group, a heptadecafluorodecyl group, a pentafluoropropyl group, a tetradecafluorooctyl group, a pentadecafluorooctyl group, an octadecafluorodecyl group, and a nonadecafluorodecyl. A $C_2$ to $C_8$ fluoroalkyl group is more preferable such as a trifluoroethyl group, a tetrafluoropropyl group, a hexafluoroisopropyl group, an octafluoropentyl group, and a dodecafluorooctyl group. A trifluoroethyl group is the most preferable.

The polymerizable functional group of the component B is preferably a radical polymerizable functional group and more preferably one having a carbon-carbon double bond. Preferable examples include a vinyl group, an allyl group, a (meth)acryloyl group, α-alkoxymethyl acryloyl group, a maleic acid residue, a fumaric acid residue, an itaconic acid residue, a crotonic acid residue, a isocrotonic acid residue, and a citraconic acid residue. Among these, because of having higher polymerizability, a (meth)acryloyl group is the most preferable.

Because the effect is large of providing a low hydrous soft ophthalmic lens that has flexibility and an excellent wearing feeling and further has excellent mechanical properties such as resistance to bending, (meth)acrylic acid fluoroalkyl ester is the most preferable as the component B. Specific examples of the (meth)acrylic acid fluoroalkyl ester include trifluoroethyl (meth)acrylate, tetrafluoroethyl (meth)acrylate, trifluoropropyl (meth)acrylate, tetrafluoropropyl (meth)acrylate, pentafluoropropyl (meth)acrylate, hexafluorobutyl (meth)acrylate, hexafluoroisopropyl (meth)acrylate, heptafluorobutyl (meth)acrylate, octafluoropentyl (meth)acrylate, nonafluoropentyl (meth)acrylate, dodecafluoropentyl (meth)acrylate, dodecafluoroheptyl (meth)acrylate, dodecafluorooctyl (meth)acrylate, and tridecafluoroheptyl group (meth)acrylate. Preferably used are trifluoroethyl (meth)acrylate, tetrafluoroethyl (meth)acrylate, hexafluoroisopropyl (meth)acrylate, octafluoropentyl (meth)acrylate, and dodecafluorooctyl (meth)acrylate. Trifluoroethyl (meth)acrylate is the most preferable.

Only one type of the component B according to the present invention may be used, or two or more types thereof may be used in combination.

The content of the component B in the copolymer is, with respect to 100 parts by mass of the component A, preferably 10 to 500 parts by mass, more preferably 20 to 400 parts by mass, and further preferably 20 to 200 parts by mass. A too small amount of use of the component B tends to produce cloudiness in an ophthalmic lens obtained or make mechanical properties such as resistance to bending unsatisfactory.

As the copolymer for use in the base material, a copolymer may be used that further copolymerizes, in addition to the component B, the component M that is a monofunctional monomer having a siloxanyl group. In the present specification, the siloxanyl group means a group having a Si—O—Si bond.

The siloxanyl group of the component M is preferably linear. When the siloxanyl group of is linear, the shape recoverability of a low hydrous soft ophthalmic lens obtained increases. The linear here indicates a structure represented by a Si—(O—Si)$_{n-1}$—O—Si bond that stretches in a line with a silicon atom connected to a group having a polymerizable group as a starting point (where n represents an integer of two or more). In order for a medical device obtained to have sufficient shape recoverability, n is preferably an integer of 3 or more, more preferably 4 or more, further preferably 5 or more, and most preferably 6 or more. That "the siloxanyl group is linear" here means that the siloxanyl group has the above linear structure and does not have any Si—O—Si bond that does not satisfy the condition of the linear structure.

The base material preferably has as a main component a copolymer containing the component M whose number average molecular weight is 300 to 120,000. The main component here means a component contained in an amount of 50% by mass or more based on the mass of the base material under dry condition (100% by mass).

The number average molecular weight of the component M is preferably 300 to 120,000. When the number average molecular weight of the component M is within this range, a base material can be obtained that is flexible (low modulus), has an excellent wearing feeling, and further has excellent mechanical properties such as resistance to bending. Because of being capable of obtaining a base material that has more excellent mechanical properties such as resistance to bending and has excellent shape recoverability, the number average molecular weight of the component M is preferably 500 or more. The number average molecular weight of the component M is more preferably in a range of 1,000 to 25,000, and further preferably in a range of 5,000 to 15,000. A too low number average molecular weight of the component M tends to decrease mechanical properties such as resistance to bending tend, and in particular, when it is less than 500, resistance to bending and shape recoverability may decrease. A too high number average molecular weight of the component M is unfavorable, because flexibility and transparency tend to decrease.

The polymerizable functional group of the component M is preferably a radical polymerizable functional group and more preferably one having a carbon-carbon double bond. Preferable examples of the polymerizable functional group include a vinyl group, an allyl group, a (meth)acryloyl group, α-alkoxymethyl acryloyl group, a maleic acid residue, a fumaric acid residue, an itaconic acid residue, a crotonic acid residue, a isocrotonic acid residue, and a citraconic acid residue. Among these, because of having higher polymerizability, a (meth)acryloyl group is the most preferable.

The component M preferably has a structure of Formula (ML1) below:

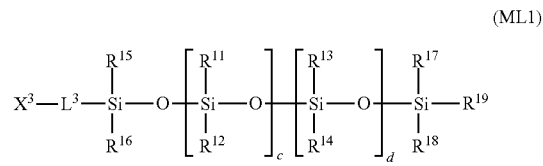

(ML1)

In Formula (ML1), $X^3$ represents a polymerizable functional group. $R^{11}$ to $R^{19}$ each independently represent a substituent selected from a hydrogen atom, a $C_1$ to $C_{20}$ alkyl group, a phenyl group, and a $C_1$ to $C_{20}$ fluoroalkyl group. L3 represents a divalent group. The symbols c and d each independently represent an integer of 0 to 700, where c and d are not simultaneously zero.

X3 is preferably a radical polymerizable functional group and is preferably one having a carbon-carbon double bond. Preferable examples of the polymerizable functional group include a vinyl group, an allyl group, a (meth)acryloyl group, α-alkoxymethyl acryloyl group, a maleic acid residue, a fumaric acid residue, an itaconic acid residue, a crotonic acid residue, a isocrotonic acid residue, and a citraconic acid residue. Among these, because of having higher polymerizability, a (meth)acryloyl group is the most preferable.

Because of being likely to obtain a low hydrous soft ophthalmic lens having favorable mechanical properties, the polymerizable functional group of the component M is preferably copolymerizable with the polymerizable functional group of the component A, and because of being likely to obtain a low hydrous soft ophthalmic lens having favorable surface characteristics owing to the component M and the component A uniformly copolymerized, the polymerizable functional group of the component M is preferably the same as the polymerizable functional group of the component A.

Specific preferable examples of $R^{11}$ to $R^{19}$ include: a hydrogen atom; a $C_1$ to $C_{20}$ alkyl group such as a methyl group, en ethyl group, a propyl group, an isopropyl group, a butyl group, a t-butyl group, a decyl group, a dodecyl group, and octadecyl group; and a $C_1$ to $C_{20}$ fluoroalkyl group such as a phenyl group, a trifluoromethyl group, a trifluoroethyl group, a trifluoropropyl group, a tetrafluoropropyl group, a hexafluoroisopropyl group, a pentafluorobutyl group, a heptafluoropentyl group, a nonafluorohexyl group, a hexafluorobutyl group, a heptafluorobutyl group, an octafluoropentyl group, a nonafluoropentyl group, a dodecafluoroheptyl group, a tridecafluoroheptyl group, a dodecafluorooctyl group, a tridecafluorooctyl group, a hexadecafluorodecyl group, a heptadecafluorodecyl group, a pentafluoropropyl group, a tetradecafluorooctyl group, a pentadecafluorooctyl group, an octadecafluorodecyl group, and a nonadecafluorodecyl group. Among these, in view of imparting favorable mechanical properties and high oxygen permeability to a low hydrous soft ophthalmic lens, a hydrogen atom and a methyl group are more preferable, and a methyl group is the most preferable.

$L^3$ is preferably a $C_1$ to $C_{20}$ divalent group. Among these, because of having the advantage of being likely to obtain the compound (ML1) in high purity, $L^3$ is preferably groups represented by Formulae (LE1) to (LE12) below. Among these, groups represented by Formulae (LE1), (LE3), (LE9), and (L11) below are more preferable, groups represented by Formulae (LE1) and (LE3) below are further preferable, and a group represented by Formula (LE1) below is the most preferable. Formulae (LE1) to (LE12) below are represented with the left side as an end bonded to the polymerizable functional group $X^3$ and with the right side as an end bonded to a silicon atom.

$OCH_2CH_2CH_2$ (LE1)

$NHCH_2CH_2CH_2$ (LE2)

$OCH_2CH_2NHCOOCH_2CH_2CH_2$ (LE3)

$OCH_2CH_2NHCONHCH_2CH_2CH_2$ (LE4)

$OCH_2CH_2CH_2CH_2$ (LE5)

$NHCH_2CH_2CH_2CH_2$ (LE6)

$OCH_2CH_2NHCOOCH_2CH_2CH_2CH_2$ (LE7)

$OCH_2CH_2NHCONHCH_2CH_2CH_2CH_2$ (LE8)

$OCH_2CH_2OCH_2CH_2CH_2$ (LE9)

$NHCH_2CH_2OCH_2CH_2CH_2$ (LE10)

$OCH_2CH_2NHCOOCH_2CH_2OCH_2CH_2CH_2$ (LE11)

$OCH_2CH_2NHCONHCH_2CH_2OCH_2CH_2CH_2$ (LE12)

In Formula (ML1), the sum of c and d (c+d) is preferably 3 or more, more preferably 10 or more, more preferably 10 to 500, more preferably 30 to 300, and further preferably 50 to 200.

When $R^{11}$ to $R^{18}$ are all a methyl group, d=0, and c is preferably 3 to 700, more preferably 10 to 500, more preferably 30 to 300, and further preferably 50 to 200. In this case, the value of c is determined by the molecular weight of the component M.

In the base material of the low hydrous soft ophthalmic lens according to the present invention, one type of the component M may be used, or two or more types thereof may be used in combination.

The base material of the low hydrous soft ophthalmic lens according to the present invention contains the component M in an appropriate amount, leading to reduced cross-link density and increased degree of freedom of the polymer, thereby achieving an appropriately soft and low-modulus base material. In contrast, a too low content of the component M increases the cross-link density, thereby making the base material hard. A too high content of the component M is unfavorable, because the base material becomes too soft to be likely to be broken.

In the base material of the low hydrous soft ophthalmic lens according to the present invention, it is preferable for the mass ratio between the component M and the component A that the component M is, with respect to 100 parts by mass of the component A, 5 to 200 parts by mass, more preferably 7 to 150 parts by mass, and most preferably 10 to 100 parts by mass. A content of the component M being less than 5 parts by mass with respect to 100 parts by mass of the component A increases the cross-link density, thereby making the base material hard. A content of the component M exceeding 200 parts by mass with respect to 100 parts by mass of the component A is unfavorable, because the base material becomes too soft to be likely to be broken.

The low hydrous soft ophthalmic lens according to the present invention forms a layer (hereinafter, called a coating layer) formed of a hydrophilic polymer at least on the surface of the base material, and at least part of the inside of the layer is cross-linked, and the cross-links are preferably formed by the irradiation with radiation. In the low hydrous soft ophthalmic lens according to the present invention, the base material and the layer may cross-link therebetween at least partially. This can provide the surface of the lens with favorable wettability and slidability and provide an excellent wearing feeling. However, the irradiation with radiation can produce cross-links also in part of the inside of the base material at the same time. Excessive cross-links produced in the base material are unfavorable, because the modulus of elasticity of the base material increases and flexibility is impaired. However, because the material of the base material of the low hydrous soft ophthalmic lens according to the present invention contains an appropriate amount of the component M, thereby providing the advantages of increasing the degree of freedom of the polymer along with reduced cross-linking density, reducing an excessive increase in the modulus of elasticity of the base material when irradiated with radiation, and obtaining a moderately soft, low-modulus base material.

When the component C, which is a component different from the component A, the component B, and the component M, is used as the copolymer for use in the base material as described above, the component C is preferably ones that reduce the glass transition point of the copolymer to a room temperature or 0° C. or less. They reduce cohesive energy, thereby producing the effect of proving the copolymer with rubber elasticity and softness.

The polymerizable functional group of the component C is preferably a radical polymerizable functional group and more preferably one having a carbon-carbon double bond. Preferable examples of the polymerizable functional group include a vinyl group, an allyl group, a (meth)acryloyl group, α-alkoxymethyl acryloyl group, a maleic acid residue, a fumaric acid residue, an itaconic acid residue, a crotonic acid residue, a isocrotonic acid residue, and a citraconic acid residue. Among them, because of having higher polymerizability, a (meth)acryloyl group is the most preferable.

In order to improve flexibility and mechanical properties such as resistance to bending, preferable examples of the component C is (meth)acrylic acid alkyl ester and preferably (meth)acrylic acid alkyl ester having a $C_1$ to $C_{20}$ alkyl group. Specific examples thereof include methyl (meth)acrylate, ethyl (meth)acrylate, n-propyl (meth)acrylate, n-butyl (meth)acrylate, tert-butyl (meth)acrylate, isobutyl (meth) acrylate, n-hexyl (meth)acrylate, n-octyl (meth)acrylate, 2-ethylhexyl (meth)acrylate, n-heptyl (meth)acrylate, n-nonyl (meth)acrylate, n-decyl (meth)acrylate, isodecyl (meth)acrylate, n-lauryl (meth)acrylate, tridecyl (meth)acrylate, n-dodecyl (meth)acrylate, cyclopentyl (meth)acrylate, cyclohexyl (meth)acrylate, and n-stearyl (meth)acrylate. More preferable are n-butyl (meth)acrylate, n-octyl (meth) acrylate, n-lauryl (meth)acrylate, and n-stearyl (meth)acrylate. Among these, further preferable is (meth)acrylic acid alkyl ester having a $C_1$ to $C_{10}$ alkyl group. A too large number of carbons of the alkyl group is unfavorable, because the transparence of a lens obtained may decrease.

In order to improve mechanical properties, surface wettability, and the dimensional stability of a lens, a monomer described below can be copolymerized as the component C as needed. Examples of a monomer for improving mechanical properties include aromatic vinyl compounds such as styrene, tert-butyl styrene, and α-methyl styrene.

Examples of a monomer for improving surface wettability include methacrylic acid, acrylic acid, itaconic acid, 2-hydroxyethyl methacrylate, 2-hydroxyethyl acrylate, 2-hydroxypropyl methacrylate, 2-hydroxypropyl acrylate, glycerol methacrylate, polyethylene glycol methacrylate, N,N-dimethyl acrylamide, N-methyl acrylamide, dimethylaminoethyl methacrylate, methylenebisacrylamide, diacetone acrylamide, N-vinylpyrrolidone, N-vinylcaprolactam, N-vinylacetamide, and N-vinyl-N-methylacetamide. Among these, a monomer having an amido group is preferable such as N,N-dimethyl acrylamide, N-methyl acrylamide, dimethylaminoethyl methacrylate, methylenebisacrylamide, diacetone acrylamide, N-vinylpyrrolidone, N-vinylcaprolactam, N-vinylacetamide, and N-vinyl-N-methylacetamide.

Examples of a monomer for improving the dimensional stability of a lens include ethylene glycol dimethacrylate, diethylene glycol dimethacrylate, triethylene glycol dimethacrylate, polyethylene glycol dimethacrylate, trimethylolpropane trimethacrylate, pentaerythritol tetramethacrylate, bisphenol A dimethacrylate, vinyl methacrylate, acryl methacrylate, acrylates corresponding to theses methacrylates, divinyl benzene, and triarylisocyanulate.

One type of the component C may be used, or two or more types thereof may be used in combination.

The amount of use of the component C is, with respect to 100 parts by mass of the component A, preferably 0.001 to 400 parts by mass, more preferably 0.01 to 300 parts by mass, further preferably 0.01 to 200 parts by mass, and most preferably 0.01 to 30 parts by mass. A too small amount of use of the component C makes it difficult to obtain the effects expected by the component C. A too large amount of use of the component C tends to produce cloudiness in an ophthalmic lens obtained or make mechanical properties such as resistance to bending unsatisfactory.

The low hydrous soft ophthalmic lens according to the present invention may further contain components such as ultraviolet absorbers, dyes, coloring agents, wetting agents, slipping agents, medicines and dietary supplements, compatibilizers, antibacterial components, and mold release agents. Any of the above components can be contained in a non-reactive manner or in a copolymerizing manner.

When an ultraviolet absorber is contained, the eyes of a wearer of an ophthalmic lens can be protected from harmful ultraviolet rays. When a dye is contained, an ophthalmic lens is colored, which facilitates identification, thereby improving convenience in handling.

Any of the above components can be contained in a non-reactive manner or in a copolymerizing manner. When any of the above components is copolymerized, that is, when an ultraviolet absorber having a polymerizable group, a coloring agent having a polymerizable group, and the like are used, the component is copolymerized with the base material and is fixed thereto, and the possibility of elution is reduced, which is favorable.

The base material is preferably formed of a component selected from ultraviolet absorbers and coloring agents and two or more kinds of components C (hereinafter, components Ck) other than these. In this case, it is preferable as the components Ck that at least one is selected from $C_1$ to $C_{10}$ (meth)acrylic acid alkyl ester and at least one is selected from the above-described monomers for improving the surface wettability. Using two or more kinds of components Ck increases the affinity with an ultraviolet absorber and a coloring agent and makes it easy to obtain a transparent base material.

When using an ultraviolet absorber, its amount of use is, with respect to 100 parts by mass of the component A, preferably 0.01 to 20 part by mass, more preferably 0.05 to 10 parts by mass, and further preferably 0.1 to 2 parts by mass. When using a coloring agent, its amount of use is, with respect to 100 parts by mass of the component A, preferably 0.00001 to 5 part by mass, more preferably 0.0001 to 1 parts by mass, and further preferably 0.0001 to 0.5 parts by mass. A too low content of the ultraviolet absorber and the coloring agent makes it difficult to obtain an ultraviolet absorbing effect and a coloring effect. In contrast, a too high content thereof makes it difficult to dissolve these components in the base material. The amount of use of each of the components Ck is, with respect to 100 parts by mass of the component A, preferably 0.1 to 100 parts by mass, more preferably 1 to 80 parts by mass, and further preferably 2 to 50 parts by mass. A too small amount of use of the components Ck tends to make it difficult to obtain a transparent base material, because of a shortage of affinity with the ultraviolet absorber and the coloring agent. A too large amount of use of the components Ck tends to produce cloudiness in an ophthalmic lens obtained or make mechanical properties such as resistance to bending unsatisfactory, which is unfavorable.

The degree of cross-linking of the base material of the low hydrous soft ophthalmic lens according to the present invention is preferably in a range of 2.0 to 18.3. The degree of cross-linking is represented by Formula (Q1) below:

$$\text{Degree of cross-linking} = \frac{\sum_{n=1}^{\infty} \{Qn \times (n-1)\}}{\sum_{n=1}^{\infty} Wn} \quad (Q1)$$

In Formula (Q1), Qn represents the total millimolar amount of a monomer having n polymerizable groups per molecule, and Wn represents the total mass (kg) of the monomer having n polymerizable groups per molecule. When the molecular amount of the monomer has distribution, the millimolar amount is calculated using the number average molecular weight.

The degree of cross-linking of the base material according to the present invention being less than 2.0 makes handling difficult, because of being too soft. The degree of cross-linking exceeding 18.3 is unfavorable, because a wearing feeling tends to worse, because of being too hard. The degree of cross-linking is more preferably in a range of 3.5 to 16.0, further preferably in a range of 8.0 to 15.0, and most preferably in a range of 9.0 to 14.0.

Any known method can be used for a method for manufacturing the base material of the low hydrous soft ophthalmic lens, that is, a lens-shaped molded body. Examples of the method include a method in which a round bar-shaped or plate-shaped polymer is temporarily formed, and it is cut into a desired shape by machining or the like, mold polymerization, and spin casting polymerization. When a lens is formed by machining, refrigerated machining at a low temperature is preferable.

Described next as an example is a method for manufacturing an ophthalmic lens by polymerizing a raw composition containing the component A by mold polymerization. First, a cavity between two mold members having a definite shape is filled with the raw composition. Examples of the material of the mold members include resin, glass, ceramics, and metal. When performing photopolymerization, resin or glass is preferably used, because optically transparent materials are preferable. For some shapes of the mold members and characteristics of the raw composition, a gasket may be used in order to give an ophthalmic lens certain thickness and prevent the raw composition filled in the cavity from leaking. The mold whose cavity has been filled with the raw composition is irradiated with active rays such as ultraviolet rays, visible rays, or a combination thereof or heated in an oven or a liquid tank, thereby polymerizing the filling raw composition. Two polymerization methods may be used in combination. In other words, thermal polymerization may be performed after photopolymerization, or photopolymerization may be performed after thermal polymerization. A specific aspect of photopolymerization includes irradiation with light containing ultraviolet rays such as the light of a mercury lamp and a UV lamp (e.g., FL15BL, Toshiba) for a short period of time (generally less than one hour). When performing thermal polymerization, preferable conditions include heating a composition from around a room temperature gradually up to a temperature in a range between 60° C. and 200° C. over a few hours to a few tens of hours, in order to maintain the optical uniformity and quality of the ophthalmic lens and increase reproducibility.

During polymerization, it is preferable to add a thermal polymerization initiator or a photopolymerization initiator represented by peroxides and azo compounds in order to facilitate polymerization. When performing thermal polymerization, selected is one having optimum decomposition characteristics at a desired reaction temperature. Generally, preferably examples include an azo-based initiator or a peroxide-based initiator having a 10-hour half-life temperature of 40 to 120° C. Examples of a photoinitiator when performing photopolymerization include carbonyl compounds, peroxides, azo compounds, sulfur compounds, halogen compounds, and metallic salts thereof. These polymerization initiators may be used singly or used in combination. The amount of a photopolymerization is preferably 5% by mass at the most with respect to a polymerization mixture.

When polymerizing, a polymerization solvent may be used. As the solvent, various solvents may be used including organic and inorganic solvents. Examples of the solvent include: water; alcohol solvents such as methyl alcohol, ethyl alcohol, n-propyl alcohol, isopropyl alcohol, n-butyl alcohol, isobutyl alcohol, t-butyl alcohol, t-amyl alcohol, tetrahydrolinalool, ethylene glycol, diethylene glycol, triethylene glycol, tetraethylene glycol, and polyethylene glycol; glycol ether solvents such as methyl cellosolve, ethyl cellosolve, isopropyl cellosolve, butyl cellosolve, propylene glycol monomethyl ether, diethylene glycol monomethyl ether, triethylene glycol monomethyl ether, polyethylene glycol monomethyl ether, ethylene glycol dimethyl ether, diethylene glycol dimethyl ether, triethylene glycol dimethyl ether, and polyethylene glycol dimethyl ether; ester solvents such as ethyl acetate, butyl acetate, amyl acetate, ethyl lactate, and methyl benzoate; aliphatic hydrocarbon solvents such as n-hexane, n-heptane, and n-octane; alicyclic hydrocarbon solvents such as cyclohexane, and ethyl cyclohexane; ketone solvents such as acetone, methyl ethyl ketone, and methyl isobutyl ketone; aromatic hydrocarbon solvents such as benzene, toluene, and xylene; and petroleum solvents. Only one type of these solvents may be used, or two or more types thereof may be used in combination.

The low hydrous soft ophthalmic lens according to the present invention forms a layer (hereinafter, called a coating layer) formed of a hydrophilic polymer such as an acidic polymer and a basic polymer on at least part of the surface of the base material. At least one type of these hydrophilic polymers preferably contains nitrogen atoms and no silicon atom.

In view of surface wettability and slidability, preferable examples of the hydrophilic polymer include polyvinylpyrrolidone, polyacrylamide, polydimethylacrylamide, poly(N-methylvinylacetamide), polyalkylene glycol, polyvinyl alcohol, polyvinyl acetate, polyvinyl caprolactam, cellulose derivatives, and polysaccharides. Although the above examples are mainly homopolymers, copolymers thereof are also preferable.

Among the hydrophilic polymers, acidic polymers and basic polymers are particularly preferable.

As a preferable example, when acidic polymers and basic polymers are used, it is preferably that at least one acidic polymer and at least one basic polymer contain nitrogen atoms and do not any silicon atom. It is more preferable that all the acidic polymers and the basic polymers do not contain any silicon atom. "Contain" here refers to containing or not containing as an atom constituting the polymers and does not intend any atom contained in a compound that is simply mixed with these polymers or atom contained in solvents of these polymers. In any case, used is one whose nitrogen element content in the coating layer is higher than the nitrogen element content of the silicon-containing base material. The "layer" in the present invention means a molecular aggregate formed on the surface of the base material. The "layer" in the present invention does not necessarily have a uniform structure in the plane direction and in the depth direction microscopically and does not necessarily have a structure in which polymers are stacked in a flat manner. For example, the layer in the present invention may have a part in which the acidic polymer and/or the basic polymer are not present. Any two or more among the acidic polymer, the basic polymer, and the base material may be present in a mixed manner or no clear inter-layer boundary may be present.

The thickness of the layer formed of the hydrophilic polymer is preferably 100 μm or less, more preferably 10 μm or less, further preferably 1 μm or less, and particularly preferably 0.5 μm or less, because being too thick is likely to bring about optical unevenness. The thickness of the layer formed of the hydrophilic polymer is preferably 0.1 nm or more, more preferably 1 nm or more, further preferably 10 nm or more, and particularly preferably 50 nm or more, because being too thin is likely to bring about a shortage of the hydrophilicity of the surface. The thickness of the layer formed of the hydrophilic polymer means thickness under the dry condition and can be determined by a method such as electron microscopy.

The coating layer is cross-linked in at least part of the inside of the layer. The base material and the coating layer may cross-link therebetween at least partially. Cross-link here refers to the bonding of polymers with a bridging structure through their own functional groups or cross-linking agents.

The present invention can adopt either one of the following (1) and (2) or a combination thereof as a method for determining that the coating layer is cross-linked.

(1) Whether at least part of the inside of the layer is cross-linked is determined by an instrumental analytical method.

(2) The polymer contained in the coating layer is dissolved in a solvent or solution that can dissolve the polymer alone, and insolubles containing cross-linked products of the polymer are observed.

A model molded body of the coating layer may be exposed to the same conditions (or substantially the same conditions) as the process in which cross-links are formed in the coating layer, and thereafter, the presence or absence of cross-links may be determined by the above (1) or (2) method. Examples of the model molded body of the coating layer include a film-shaped molded body (a molded body I) of the polymer contained in the coating layer. As another example, the molded body I may be formed on a film-shaped molded body (a molded body II) of the same (or substantially the same) material as the base material. The latter model molded body is useful for determining that the base material and the coating layer cross-link therebetween.

The cross-links are preferably produced by irradiating the base material with at least the hydrophilic polymer attached with radiation. The radiation is preferably various kinds of ionic rays, electron rays, positron rays, X-rays, gamma rays, or neutron rays, more preferably electron rays or gamma rays, and most preferably gamma rays.

The cross-links are produced in the inside of the coating layer or between the coating layer and the base material as described above, thereby providing the above-described resistance to rubbing for cleaning, and further, providing the surface of a lens with favorable wettability and slidability, and providing an excellent wearing feeling.

The low hydrous soft ophthalmic lens according to the present invention has extremely excellent slidability or excellent slidability (about intermediate between medium slidability and extremely excellent slidability) in a sensitivity evaluation in which a test piece shaped in a contact lens form is immersed into a borate buffer solution and is then pulled up from the borate buffer solution, and it is rubbed with a forefinger a predetermined number of times.

The low hydrous soft ophthalmic lens according to the present invention has wettability at least to the extent that in visual observation, when a test piece shaped in a contact lens form is immersed into a borate buffer solution, pulled up from the borate buffer solution, and held in the air so that its diameter direction is vertically directed, on the appearance of the surface, a liquid film on the surface is held for 5 seconds or more then drains. The diameter here is the diameter of a circle formed by the perimeter of the ophthalmic lens.

The low hydrous soft ophthalmic lens according to the present invention can provide the surface of the lens with sufficient wettability, slidability, and antifouling property by forming the coating layer formed of the hydrophilic polymer on the surface, in spite of being low hydrous and soft, and even when the base material is neutral. This can remarkably reduce or avoid a phenomenon in which a lens sticks to a cornea when worn.

The coating layer of the low hydrous soft ophthalmic lens according to the present invention does not need to have covalent bonding with the base material. Because manufacture by a simple process is enabled, the coating layer does not preferably have covalent bonding with the base material. Even when the coating layer does not have covalent bonding with the base material, it has practical durability.

The durability of a low hydrous soft ophthalmic lens is, for example, evaluated as follows: A sample (shaped in a contact lens form) is placed in a recess formed on a palm of an adult man, and given cleaning fluid is added thereto as needed. Both sides of the sample are rubbed 10 times each with the ball of the forefinger of the other hand. After that, with the sample immersed into a borate buffer solution, the wettability, slidability, and the amount of coating are determined. When the coating layer irradiated with radiation is formed on the surface of the low hydrous soft ophthalmic lens, favorable wettability and slidability are given even after performing the above-described rubbing treatment. The above rubbing method is set considering an estimated use method of a contact lens.

The coating layer of the low hydrous soft ophthalmic lens according to the present invention is formed by treating the surface of the base material with a hydrophilic polymer solution ("solution" means an aqueous solution) described below in detail. The aqueous solution here is a solution with water as a main component.

The hydrophilic polymer solution according to the present invention generally means a solution containing one type of polymer. (One type means a polymer group manufactured by one synthesis reaction. Even with one type of (the same) polymer, solutions that differ in concentration are not regarded as one type. Even with the same constituent monomer species, polymers synthesized with varied blending ratios are not one type).

The coating layer is preferably formed of one or more types of acidic polymers and one or more types of basic polymers. It is more preferable that two or more types of acidic polymers or two or more types of basic polymers are used, because characteristics such as slidability and antifouling property are likely to be produced on the surface of the ophthalmic lens. It is further preferable that particularly two or more types of acidic polymers and one or more types of basic polymers are used, because the above tendency is strengthened.

The coating layer is preferably formed by performing treatment with one or more types of acidic polymer solutions once or more times and treatment with one or more types of basic polymer solutions once or more times.

The coating layer is formed on the surface of the base material by performing treatment with one or more types of acidic polymer solutions and treatment with one or more types of basic polymer solutions preferably once to five times each, more preferably once to three times each, and further preferably once to twice each. The number of times of the treatment with the acidic polymer solutions and the number of times of the treatment with the basic polymer solutions may be different from each other.

The low hydrous soft ophthalmic lens according to the present invention can provide excellent wettability and slidability by an extremely small number of times, or a total of twice or three times, of the treatment with one or more types of acidic polymer solutions and the treatment with one or more types of basic polymer solutions. This is of great technical significance in view of the shortening of the manufacturing process. In that sense, in the low hydrous soft ophthalmic lens according to the present invention, the total number of times of the treatment with the acidic polymer solutions and the treatment with the basic polymer solutions is preferably twice or three times.

It is preferable to perform treatment with two types of acidic polymer solutions once each and treatment with the basic polymer solution once on the coating layer of the low hydrous soft ophthalmic lens according to the present invention.

The inventors have confirmed that performing only treatment with either one of the acidic polymer solution and the basic polymer solution on the coating layer produces almost no wettability and slidability.

As the basic polymer, a homopolymer or a copolymer having a plurality of basic groups along a polymer chain can be used. The basic group is preferably an amino group or its salt. Preferable examples of such a basic polymer include poly(allylamine), poly(vinylamine), poly(ethyleneimine), poly(vinylbenzyl trimethylamine), polyaniline, poly(aminostyrene), an amino group-containing (meth)acrylate polymer such as poly(N,N-dialkylaminoethyl methacrylate), an amino group-containing (meth)acrylamide polymer such as poly(N,N-dimethylaminopropyl acrylamide), and salts thereof. Although the above examples are homopolymers, copolymers thereof (i.e., a copolymer of basic monomers constituting the above basic polymers or a copolymer of a basic monomer and another monomer) may also be preferably used.

When the basic polymer is a copolymer, in view of a high degree of polymerization, the basic monomer constituting the copolymer is preferably a monomer having an allyl group, a vinyl group, or a (meth)acryloyl group and most preferably a monomer having a (meth)acryloyl group. Preferable examples of the basic monomer constituting the copolymer include allylamine, vinylamine (N-vinylcarboxylic acid amide as the precursor), vinylbenzyl trimethylamine, amino group-containing styrene, amino group-containing (meth)acrylate, amino group-containing (meth)acrylamide, and salts thereof. Among these, in view of a high degree of polymerization, more preferable are amino group-containing (meth)acrylate, amino group-containing (meth)acrylamide, and salts thereof, and the most preferable are N,N-dimethylaminoethyl methacrylate, N,N-dimethylaminopropyl acrylamide, and salts thereof.

The basic polymer may be a polymer having a quaternary ammonium structure. A polymer compound having the quaternary ammonium structure, when used in the coating of a soft ophthalmic lens, can provide the soft ophthalmic lens with antimicrobial property.

As the acidic polymer, a homopolymer or a copolymer having a plurality of acidic groups along a polymer chain can be used. The acidic group is preferably a carboxy group, a sulfone group, or salts thereof and most preferably a carboxy group and its salts. Preferable examples of such an acidic polymer include polymethacrylic acid, polyacrylic acid, poly(vinyl benzoic acid), poly(thiophene-3-acetic acid), poly(4-styrenesulfonic acid), polyvinylsulfonic acid, poly(2-acrylamide-2-methylpropanesulfonic acid), and salts thereof. Although the above examples are homopolymers, copolymers thereof (i.e., a copolymer of acidic monomers constituting the above acidic polymers or a copolymer of an acidic monomer and another monomer) may also be preferably used.

When the acidic polymer is a copolymer, the acidic monomer constituting the copolymer is preferably a monomer having an allyl group, a vinyl group, or a (meth)acryloyl group and most preferably a monomer having a (meth)acryloyl group in view of a high degree of polymerization. Preferable examples of the acidic monomer constituting the copolymer include (meth)acrylic acid, vinyl benzoic acid, styrenesulfonic acid, vinylsulfonic acid, 2-acrylamide-2-methylpropanesulfonic acid, and salts thereof. Among these, more preferable are (meth)acrylic acid, 2-acrylamide-2-methylpropanesulfonic acid, and salts thereof, and the most preferable are (meth)acrylic acid and salts thereof.

At least one type of the basic polymers and the acidic polymers is preferably a polymer having a group selected from an amido group and a hydroxy group. It is preferable that the basic polymers and/or the acidic polymers have an amido group, because a surface having not only wettability but also slidability can be formed. It is preferable that the basic polymers and/or the acidic polymers have a hydroxy group, because a surface having not only wettability but also antifouling property against lacrimal fluid can be formed.

It is more preferable that two or more types of the acidic polymers and the basic polymers are polymers having a group selected from a hydroxy group and amido group. In other words, it is preferable that the low hydrous soft ophthalmic lens contains two or more types of polymers selected from the acidic polymer having a hydroxy group, the basic polymer having a hydroxy group, the acidic polymer having an amido group, and the basic polymer having the amido group. This case is preferable, because the effect of forming a surface having slidability or the effect of forming a surface having excellent antifouling property against lacrimal fluid can be produced more remarkably.

It is further preferable that the coating layer contains at least one type of polymer selected from the acidic polymer having a hydroxy group and the basic polymer having a hydroxy group and at least one type of polymer selected from the acidic polymer having an amido group and the basic polymer having an amido group. This case is preferable, because both the effect of forming a surface having slidability and the effect of forming a surface having excellent antifouling property against lacrimal fluid can be produced.

Examples of the basic polymer having an amido group include polyamides having an amino group, partially-hydrolyzed chitosan, a copolymer of a basic monomer and a monomer having an amido group.

Examples of the acidic polymer having an amido group include polyamides having a carboxy group and a copolymer of an acidic monomer and a monomer having an amido group.

Examples of the basic polymer having a hydroxy group include amino-polysaccharides such as chitin and a copolymer of a basic monomer and a monomer having a hydroxy group.

Examples of the acidic polymer having a hydroxy group include: polysaccharides having an acidic group such as hyaluronic acid, chondroitin sulfuric acid, carboxymethylcellulose, and carboxypropylcellulose; and a copolymer of an acidic monomer and a monomer having an amido group.

The monomer having an amido group is preferably a monomer having a (meth)acrylamide group or N-vinyl carboxylic acid amide (including a cyclic one) in view of the easiness of polymerization. Preferable examples of the monomer include N-vinylpyrrolidone, N-vinylcaprolactam, N-vinylacetamide, N-methyl-N-vinylacetamide, N-vinyl formamide, N,N-dimethyl acrylamide, N,N-diethyl acrylamide, N-isopropyl acrylamide, N-(2-hydroxyethyl)acrylamide, acryloyl morpholine, and acrylamide. Among these, in view of slidability, more preferable are N-vinylpyrrolidone or N,N-dimethyl acrylamide and the most preferable is N,N-dimethyl acrylamide.

Preferable examples of the monomer having a hydroxy group include hydroxyethyl (meth)acrylate, hydroxypropyl (meth)acrylate, hydroxybutyl (meth)acrylate, hydroxyethyl (meth)acrylamide, glycerol (meth)acrylate, caprolactone-modified 2-hydroxyethyl methacrylate, N-(4-hydroxyphenyl) maleimide, hydroxystyrene, and vinyl alcohol (vinyl carboxylate as the precursor). In view of the easiness of polymerization, the monomer having a hydroxy group is preferably a monomer having a (meth)acryloyl group and more preferably a (meth)acrylate monomer. Among these, in view of antifouling property against lacrimal fluid, preferable are hydroxyethyl (meth)acrylate, hydroxypropyl (meth)acrylate, and glycerol (meth)acrylate, and the most preferable is hydroxyethyl (meth)acrylate.

Specific preferable examples of the copolymer of the basic monomer and the monomer having an amido group include N,N-dimethylaminoethyl methacrylate/N-vinylpyrrolidone copolymer, N,N-dimethylaminoethyl methacrylate/N,N-dimethyl acrylamide copolymer, N,N-dimethylaminopropyl acrylamide/N-vinylpyrrolidone copolymer, and N,N-dimethylaminopropyl acrylamide/N,N-dimethyl acrylamide copolymer. The most preferable is N,N-dimethylaminopropyl acrylamide/N,N-dimethyl acrylamide copolymer.

Specific preferable examples of the copolymer of the acidic monomer and the monomer having an amido group include (meth)acrylic acid/N-vinylpyrrolidone copolymer, (meth)acrylic acid/N,N-dimethyl acrylamide copolymer, 2-acrylamide-2-methylpropanesulfonic acid/N-vinylpyrrolidone copolymer, and 2-acrylamide-2-methylpropanesulfonic acid/N,N-dimethyl acrylamide copolymer. The most preferable is (meth)acrylic acid/N,N-dimethyl acrylamide copolymer.

Specific preferable examples of the copolymer of the basic monomer and the monomer having a hydroxy group include N,N-dimethylaminoethyl methacrylate/hydroxyethyl (meth)acrylate copolymer, N,N-dimethylaminoethyl methacrylate/glycerol (meth)acrylate copolymer, N,N-dimethylaminopropyl acrylamide/hydroxyethyl (meth)acrylate copolymer, and N,N-dimethylaminopropyl acrylamide/glycerol (meth)acrylate copolymer. The most preferable is N,N-dimethylaminoethyl methacrylate/hydroxyethyl (meth)acrylate copolymer.

Examples of the copolymer of the acidic monomer and the monomer having a hydroxy group include (meth)acrylic acid/hydroxyethyl (meth)acrylate copolymer, (meth)acrylic acid/glycerol (meth)acrylate copolymer, 2-acrylamide-2-methylpropanesulfonic acid/hydroxyethyl (meth)acrylate copolymer, and 2-acrylamide-2-methylpropanesulfonic acid/glycerol (meth)acrylate copolymer. The most preferable is (meth)acrylic acid/hydroxyethyl (meth)acrylate copolymer.

When the copolymer of the basic monomer or the acidic monomer and the other monomer is used, the copolymerization ratio, that is, [the mass of the basic monomer or the acidic monomer]/[the mass of the other monomer] is preferably 1/99 to 99/1, more preferably 2/98 to 90/10, and further preferably 10/90 to 80/20. When the copolymerization ratio is in this range, functions such as slidability and antifouling property against lacrimal fluid are likely to be produced.

In order to change various characteristics of the coating layer, for example, thickness, the molecular weight of the acidic polymer and the basic polymer can be changed. Specifically, when the molecular weight is increased, the thickness of the coating layer generally increases. However, a too high molecular weight can increase the difficulty of handling because of increased viscosity. In view of this, the acidic polymer and the basic polymer used in the present invention preferably have a molecular weight of 2,000 to 150,000. The molecular weight is more preferably 5,000 to 100,000 and further preferably 75,000 to 100,000. The molecular weight of the acidic polymer and the basic polymer is a mass average molecular weight in terms of polyethylene glycol measured by the gel permeation chromatography (a water-based solvent).

The application of the coating layer can be achieved by many methods such as one described in, for example, WO 1999/35520, WO 2001/57118, or US Patent Application Publication No. 2001-0045676.

Described next is a method for manufacturing a low hydrous soft ophthalmic lens according to the present invention. The low hydrous soft ophthalmic lens according to the present invention is obtained by forming a coating layer by applying one or more types of acidic polymer solutions and one or more types of basic polymer solutions onto the surface of a lens-shaped molded body (base material) once to five times each, more preferably once to three times each, and further preferably once to twice each and irradiating the coating layer with radiation (preferably gamma rays). The numbers of times of the acidic polymer solution application process and the basic polymer solution application process may be different from each other.

The inventors have found that in the method for manufacturing the low hydrous soft ophthalmic lens according to the present invention can provide excellent wettability and slidability with such an extremely small number of times as a total of twice or three times of the application process of one or more types of the acidic polymer solutions and the application process of one or more types of the basic polymer solutions. This is of great technical significance in view of the shortening of the manufacturing process. In that sense, in the low hydrous soft ophthalmic lens according to the present invention, the total number of times of the application process of the acidic polymer solutions and the application process of the basic polymer solutions is preferably twice or three times.

In view of wettability, slidability, and the shortening of the manufacturing process, the application of the coating layer is preferably performed with any combination selected from combinations 1 to 4 below. Each expression below represents that the application processes are performed in order from the left on the surface of the molded body.

Combination 1: Application of a basic polymer solution/application of an acidic polymer solution Combination 2: Application of an acidic polymer solution/application of a basic polymer solution Combination 3: Application of a basic polymer solution/application of an acidic polymer solution/application of a basic polymer solution Combination 4: Application of an acidic polymer solution/application of a basic polymer solution/application of an acidic polymer solution Among these combinations, the combination 1 and the combination 4 are preferable, because a low hydrous soft ophthalmic lens obtained exhibits particularly excellent wettability.

When applying the acid polymer solution and the basic polymer solution, the surface of the base material may be untreated or treated. That the surface of the base material is treated means that the surface of the base material is subjected to surface treatment or surface modification by a known method. Preferable examples of the surface treatment or the surface modification include plasma treatment, chemical modification, chemical functionalization, and plasma coating.

A preferable aspect of the method for manufacturing a low hydrous soft ophthalmic lens according to the present invention includes a process 1 to a process 4 below in this order.

<Process 1> A process of polymerizing a monomer mixture to obtain a low hydrous, soft, lens-shaped molded body.
<Process 2> A process of bringing the molded body into contact with a basic polymer solution and rinsing off the excessive basic polymer solution.
<Process 3> A process of bringing the molded body into contact with an acidic polymer solution and rinsing off the excessive acidic polymer solution.
<Process 4> A process of irradiating the molded body with radiation.

As described above, the lens-shaped molded body is brought into contact with the acidic polymer solution and the basic polymer solution in order, thereby forming a layer formed of an acidic polymer and a basic polymer on the molded body. After that, the excessive polymers are preferably rinsed off sufficiently.

As a method for bringing the molded body into contact with the acidic polymer solution or the basic polymer solution, various coating methods can be adopted such as immersion (dipping), brush application, spray coating, spin coating, die coating, and squeezing.

When the contact with the solution is performed by immersion, the immersion time can be changed in accordance with many factors. The immersion of the molded body into the acidic polymer solution or the basic polymer solution is performed for preferably 1 to 30 minutes, more preferably 2 to 20 minutes, and most preferably 1 to 5 minutes.

The concentration of the acidic polymer solution or the basic polymer solution can be changed in accordance with the property of the acidic polymer or the basic polymer, a desired thickness of the coating layer, and many other factors. The concentration of the acidic polymer solution or the basic polymer solution is preferably 0.001 to 10% by mass, more preferably 0.005 to 5% by mass, further preferably 0.01 to 3% by mass, and most preferably 0.7 to 1.3% by mass.

The pH of the acidic polymer solution or the basic polymer solution may be maintained at preferably 2 to 5 and more preferably 2.5 to 4.5.

The rinsing off of the excessive acidic polymer solution and the basic polymer solution is performed by generally rinsing a molded body after coating with clean water or an organic solvent. The rinsing is preferably performed by immersing the molded body into water or an organic solvent or exposing the molded body to a water flow or an organic solvent flow. Although the rinsing may be completed by one process, it has been confirmed that it is effective that the rinsing process is performed a plurality number of times. The rinsing is performed over two to five processes. It is preferable to take one to three minutes for respective pieces of immersion into respective rinsing solutions.

The rinsing solution is preferably pure water, and in order to improve adhesion to the coating layer, preferably used is an aqueous solution buffered to a pH of preferably 2 to 7, more preferably 2 to 5, and further preferably 2.5 to 4.5.

A process of drying or removing an excessive rinsing solution may be included. Although the molded body is dried to some extent by simply leaving it in the atmospheric environment, drying is preferably accelerated by sending a mild air flow to the surface. The flow rate of the air flow can be adjusted as a function of the strength of a material to be dried and the mechanical fixturing of the material. The molded body does not necessarily need to be completely dried. It is of the first importance to remove droplets intimately adhering to the surface of the molded body rather than to dry the molded body. Thus, the molded body is only has to be dried to such an extent that a water or solution film on the surface of the molded body is removed, which is preferable because of leading to the shortening of process time.

The acidic polymer and the basic polymer are preferably applied alternately. They are alternately applied, thereby obtaining a low hydrous soft ophthalmic lens having excellent wettability and slidability and further an excellent wearing feeling that cannot be obtained by only either one of them.

The coating layer may be asymmetric. The "asymmetric" here refers to having different coating layers on a first side of the low hydrous soft ophthalmic lens and a second side thereof opposite the first side. The "different coating layers" here refers to the coating layer formed on the first side and the coating layer formed on the second side having different surface characteristics and functionalities.

The thickness of the coating layer can be adjusted by adding one or more salts such as sodium chloride to the acidic polymer solution or the basic polymer solution. A preferable salt concentration is 0.1 to 2.0% by mass. As the concentration of the salt increases, a polyelectrolyte takes a stereo structure closer to a sphere. However, when its concentration becomes too high, the polyelectrolyte, even if it deposits on the surface of the molded body, does not deposit favorably. A more preferable salt concentration is 0.7 to 1.3% by mass.

The irradiation of radiation may be performed with the molded body immersed into the coating solution or may be performed after the molded body is pulled out of the coating solution and rinsed. The irradiation of radiation is also preferably performed with the molded body immersed into liquid other than the coating solution. This case is preferable, because the applied radiation acts more effectively. In this case, organic and inorganic solvents may be adopted, with no specific limitation, as a solvent for the liquid for immersing the coated molded body. Examples of the solvent include: water; alcohol solvents such as methanol, ethanol, propanol, 2-propanol, butanol, tert-butanol, tert-amyl alcohol, and 3,7-dimethyl-3-octanol; aromatic hydrocarbon solvents such as benzene, toluene, and xylene; aliphatic hydrocarbon solvents such as hexane, heptane, octane, decane, petroleum ether, kerosene, ligroin, and paraffin; ketone solvents such as acetone, methyl ethyl ketone, and methyl isobutyl ketone; ester solvents such as ethyl acetate, butyl acetate, methyl benzoate, dioctyl phthalate, and ethylene glycol diacetate; ether solvents such as diethyl ether, tetrahydrofuran, dioxane; and glycol ether solvents such as ethylene glycol dialkylether, diethylene glycol dialkylether, triethylene glycol dialkylether, tetraethylene glycol dialkylether, polyethylene glycol dialkylether, polyethylene glycol-polypropylene glycol block copolymer, and polyethylene glycol-polypropylene glycol random copolymer. These solvents may be used singly or in combination. Among these, water is the most preferable. When the irradiation of radiation is performed with the molded body immersed into aqueous liquid, preferable examples of the aqueous liquid include, in addition to pure water, physiological saline, a phosphoric acid buffer solution (preferably with a pH of 7.1 to 7.3) and a boric acid buffer solution (preferably with a pH of 7.1 to 7.3).

The irradiation of radiation with the molded body hermetically sealed in a container has an advantage of capable of sterilizing the molded body at the same time.

The radiation is preferably various types of ionic rays, electron rays, positron rays, X-rays, gamma rays, and neutron rays, more preferably electron rays and gamma rays, and most preferably gamma rays. Because a too low dose of the applied radiation cannot achieve sufficient bonding between the molded body and the coating layer, the dose is preferably 1 kGy or more and more preferably 5 kGy or more. Because a too high dose of the applied radiation gives rise to deterioration of the physical properties of the molded body, the dose is preferably 40 kGy or less, preferably 25 kGy or less, and more preferably 15 kGy or less. When using gamma rays in particular, the does is preferably 25 kGy or less. This causes at least part of the inside of the coating layer to be cross-linked and causes the coating layer and the molded body to cross-link therebetween at least partially, thereby improving the durability (e.g., resistance to rubbing for cleaning) of the coating layer.

The low hydrous soft ophthalmic lens according to the present invention is suitable for ophthalmic lenses such as low hydrous soft contact lenses, intraocular lenses, artificial corneas, cornea inlays, cornea onlays, and spectacle lenses. Among these, it is particularly suitable for low hydrous soft contact lenses.

EXAMPLES

The present invention will be specifically described below by examples, but the present invention is not limited to these examples.

Analysis Methods and Evaluation Methods (1) Water Content

A test piece shaped in a contact lens form was used. The test piece was immersed into a borate buffer solution and was left at room temperature for 24 hours or more. After that, water on the surface thereof was wiped off with a wiping cloth ("Kimwipe (registered trademark)" manufactured by Nippon Paper Crecia Co., Ltd.), and the mass (Ww) thereof was measured. After that, the test piece was dried in a vacuum dryer at 40° C. for 16 hours, and the mass (Wd) thereof was measured. A water content was determined by the following formula. When the obtained value was less than 1%, the case was determined as the limit of measurement or less and was expressed as "less than 1%."

$$\text{Water content (\%)} = 100 \times (Ww - Wd)/Ww$$

(2) Wettability

A test piece shaped in a contact lens form was immersed into a borate buffer solution in a beaker at room temperature for 24 hours or more. The beaker containing the test piece and the borate buffer solution was put through an ultrasonic cleaner (for 30 seconds). The test piece was pulled up from the borate buffer solution, and the appearance of the surface thereof was visually observed when it was held so that its diameter direction was directed to be vertical. The liquid film retaining time of the surface was measured and was determined based on the following the criteria. The diameter here is the diameter of a circle formed by the perimeter of the contact lens.

A: The liquid film on the surface retains for 20 seconds or more.

B: The liquid film on the surface drains at a time of 10 seconds or more and less than 20 seconds.

C: The liquid film on the surface drains at a time of 5 seconds or more and less than 10 seconds.

D: The liquid film on the surface drains at a time of 1 second or more and less than 5 seconds.

E: The liquid film on the surface drains instantaneously (less than 1 second).

(3) Slidability

A test piece shaped in a contact lens form was immersed into a borate buffer solution in a beaker at room temperature for 24 hours or more. The beaker containing the test piece and the borate buffer solution was put through an ultrasonic cleaner (for 30 seconds). The test piece was pulled up from the borate buffer solution, and sensitivity evaluation when rubbing it with a forefinger five times was performed.

A: Extremely excellent slidability is sensed.

B: Slidability about intermediate between A and C is sensed.

C: Medium slidability is sensed.

D: Almost no slidability is sensed (about intermediate between C and E.

E: No slidability is sensed.

(4) Resistance to Rubbing for Cleaning (Examples 1 to 4)

A sample (shaped in a contact lens form) under the wet condition owing to a borate buffer solution was placed in a recess formed on a palm, and cleaning fluid ("Renu (registered trademark)", Bausch & Lomb Incorporated) was added thereto. Both sides of the sample were rubbed 10 times each with the ball of the forefinger of the other hand. After that, the sample was held between a thumb and a forefinger and both sides thereof were rubbed 20 times while pouring the cleaning fluid over the sample. The sample after rubbing for cleaning was immersed into a borate buffer solution. After that, (3) slidability evaluation was performed.

(5) Evaluation of Coating Amount

A coating amount was evaluated using the X-ray photoelectron spectroscopy (XPS). The measurement was performed under the following conditions:

Apparatus: ESCALAB220iXL

Excitation X-ray: Monochromatic Al Kα1, 2 ray (1486.6 eV)

X-ray diameter: 1 mm

Photoelectron take-off angle: 90° (the inclination of the detector with respect to the sample surface)

Position of sample measured: The vicinity of the center of a contact lens

Element information on the surface of a substance (a few nanometers) was obtained from the bond energy values of bound electrons within the substance to determine the ratio of a silicon element content with respect to a nitrogen element content (a N/Si element content ratio).

(6) Evaluation of Static Contact Angle

The evaluation of a static contact angle was performed using CONTACT-ANGLE METER (model CA-D manufactured by Kyowa Interface Science Co., Ltd).

Synthesis Examples

Described are synthesis examples of copolymers subjected to coating in examples. The molecular weights of the copolymers were measured under the following conditions:

(GPC Measurement Conditions)

Apparatus: Prominence GPC System manufactured by Shimadzu Corporation)

Pump: LC-20AD

Autosampler: SIL-20AHT

Column oven: CTO-20A

Detector: RID-10A

Column: GMPWXL (ID 7.8 mm×30 cm, particle size 13 μm) manufactured by Tosoh Corporation Solvent: Water/methanol=1/1 (with 0.1 N lithium nitrate added)

Flow rate: 0.5 mL/min

Measuring time: 30 minutes

Sample concentration: 0.1% by mass

Injection amount: 100 μL

Standard sample: Polyethylene oxide standard sample (0.1 kD to 1258 kD) manufactured by Agilent Technologies Synthesis Example 1

Pure water below indicates water purified through filtration with a reverse osmotic membrane.

<p(DMAA/AA): N,N-dimethyl acrylamide/acrylic acid (molar ratio 2/1)>

To a 500-ml three-necked flask were added N,N-dimethyl acrylamide (59.50 g, 0.600 mol), acrylic acid (21.62 g, 0.300 mol), pure water (325.20 g), a polymerization initiator VA-061 (Wako Pure Chemical Industries, Ltd., 0.1408 g, 0.562 mmol), and 2-mercapto ethanol (43.8 μL, 0.63 mmol), and to the flask were attached a three-way stopcock, a reflux condenser, a thermometer, and a mechanical stirrer. The monomer concentration was 20% by mass. The inside of the three-necked flask was deaerated by a vacuum pump and was substituted with argon three times. After that, the mixture was stirred at 50° C. for 0.5 hours, heated up to 70° C., and stirred for 6.5 hours. After the completion of polymerization, the polymerization reaction solution was condensed to 400 g by an evaporator and poured into 2-propanol/n-hexane=500 mL/500 mL to be left at rest, and the supernatant was removed through decantation. The resultant solid content was washed with 2-propanol/n-hexane=250 mL/250 mL three times. The solid content was dried by a vacuum dryer at 60° C. overnight. To the solid content was added liquid nitrogen, then it was crushed with a spatula and dried by a vacuum dryer at 60° C. for 3 hours. The molecular weight of the thus obtained copolymer was Mn: 55 kD, Mw: 192 kD (Mw/Mn=3.5).

Reference Example 1

Preparation of Coloring Agent

Twenty grams of pure water was put into a 50-mL screw cap bottle. A half grams of UniBlue A (product number 298409, Sigma-Aldrich) was added thereto and dissolved in an incubator at 37° C. After dissolution, 4 g of 1 N hydrochloric acid was added thereto, and a pH of 1 to 2 was determined with pH test paper. Twenty-four grams of ethyl acetate was added thereto, and the mixture was lightly stirred. The mixture was transferred to a 100-mL eggplant flask to be left at rest. UniBlue A moved to the ethyl acetate side, and the aqueous layer as the lower layer was thrown away. The ethyl acetate layer was transferred to a 100-mL eggplant flask, evaporated by an evaporator at 20° C., and then dried by a vacuum dryer at 40° C. for 16 hours to obtain an acid type UniBlue A [estimated structural formula (M1)].

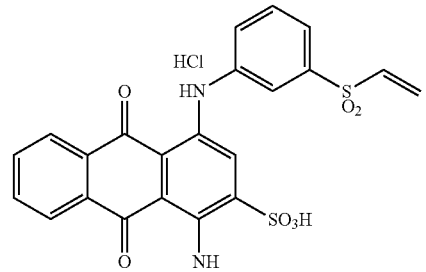

(M1)

Reference Example 2

Preparation of Coating Solution

<PAA Solution>

Polyacrylic acid (169-18591, Wako Pure Chemical Industries, Ltd., molecule weight 250,000) was dissolved in pure water to obtain a 1.2%-by-mass aqueous solution.

<PEI Solution>

Polyethylene imine (P3143, Sigma-Aldrich, molecular weight 750,000) was dissolved in pure water to obtain a 1%-by-mass aqueous solution.

<p(DMAA/AA) Solution>

The N,N-dimethyl acrylamide of Synthesis Example 1 synthesized by the inventors in the laboratory was dissolved in pure water to obtain a 1%-by-mass aqueous solution.

Reference Example 3

Mixed were polydimethylsiloxane having methacryloyl groups at both ends (FM7726, JNC, the compound of Formula (M2), mass average molecular weight 29 kD, number average molecular weight 26 kD) (50 parts by mass) as the component A, trifluoroethyl acrylate (Viscoat 3F, Osaka Organic Chemical Industry Ltd.) (45 parts by mass) as the component B, 2-ethylhexyl acrylate (3 parts by mass) as the component C, dimethylaminoethyl acrylate (1 part by mass) as the component C, an ultraviolet absorber having a polymerizable group (RUVA-93, Otsuka Chemical Co., Ltd.) (1 part by mass) as the component C, the acid type Uniblue A of Reference Example 1 (0.04 parts by mass) as the component C, a polymerization initiator "Irgacure (registered trademark)" 819 (Ciba Specialty Chemicals, 0.75 parts by mass), and t-amyl alcohol (10 parts by mass). The mixture was stirred and filtered with a membrane filter (0.45 μm) to remove insolubles and obtain a monomer mixture. This monomer mixture was put into a test tube, which was deaerated with its pressure reduced to 20 Torr (27 hPa) while it was stirred by a touch mixer and then returned to the atmospheric pressure with argon gas. This operation was repeated three times. Within a glove box in a nitrogen atmosphere, the monomer mixture was injected into a contact lens mold formed of transparent resin (propylene on the base curve side and Zeonor on the front curve side) and was irradiated with light (1.01 mW/cm², for 20 minutes) using a fluorescent lamp (Toshiba, FL-6D, daylight, 6 W, a set of four) to be polymerized. After being polymerized and immersed into a 60%-by-mass isopropyl alcohol aqueous solution together with the mold, a contact lens-shaped molded body was peeled off from the mold. The thus obtained molded body was immersed into a largely excessive amount of 80%-by-mass isopropyl alcohol aqueous solution at 60° C. for two hours. The molded body was further immersed into a largely excessive amount of 50%-by-mass isopropyl alcohol aqueous solution at room temperature (25° C.) for 30 minutes, immersed into a largely excessive amount of 25%-by-mass isopropyl alcohol aqueous solution at room temperature (same as above) for 30 minutes, and immersed into a largely excessive amount of pure water at room temperature (same as above) for two hours or more. The diameter of the perimeter of the obtained lens was about 14 mm, and the thickness at the center thereof was about 0.07 mm.

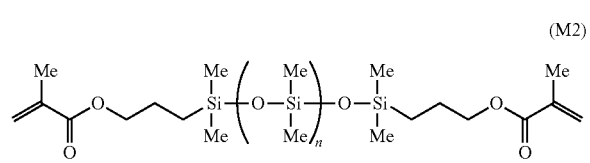

(M2)

Reference Example 4

Mixed were polydimethylsiloxane having methacryloyl groups at both ends (FM7726, JNC, the compound of Formula (M2), mass average molecular weight 29 kD, number average molecular weight 26 kD) (50 parts by mass) as the component A, trifluoroethyl acrylate (Viscoat 3F, Osaka Organic Chemical Industry Ltd.) (48.5 parts by mass) as the component B, methyl methacrylate (0.5 parts by mass) as the component C, an ultraviolet absorber having a polymerizable group (RUVA-93, Otsuka Chemical Co., Ltd.) (1 part by mass) as the component C, a polymerization initiator "Irgacure (registered trademark)" 819 (Ciba Specialty Chemicals, 0.75 parts by mass), and t-amyl alcohol (10 parts by mass). The mixture was stirred. After that, the same operations as Reference Example 3 were performed to manufacture a lens. The diameter of the perimeter of the obtained lens was about 14 mm, and the thickness at the center thereof was about 0.07 mm.

Reference Example 5

Mixed were 2-hydroxyethyl methacrylate (98 parts by mass), triethylene glycol dimethacrylate (1.0 part by mass), and a photoinitiator Irgacure 1850 (1.0 part by mass). The mixture was stirred. After that, the same operations as Reference Example 3 were performed to manufacture a lens. The diameter of the perimeter of the obtained lens was about 14 mm, and the thickness at the center thereof was about 0.07 mm.

Reference Example 6

Mixed were a silicone monomer represented by Formula (M3) (13.4 parts by mass), N,N-dimethyl acrylamide (37.0 parts by mass), a silicon monomer represented by Formula (M4) (36.6 parts by mass), a photoinitiator Irgacure 1850 (1.26 parts by mass), an ultraviolet absorber (RUVA-93, Otsuka Chemical Co., Ltd.) (1.26 parts by mass), 2-hydroxyethyl methacrylate (9.2 parts by mass), triethylene glycol dimethacrylate (1.26 part by mass), Uniblue A represented by Formula (M5) (0.02 parts by mass), and tetrahydrolinalool (23.9 parts by mass). The mixture was stirred. After that, the same operations as Reference Example 3 were performed to manufacture a lens. The diameter of the perimeter of the obtained lens was about 14 mm, and the thickness at the center thereof was about 0.07 mm.

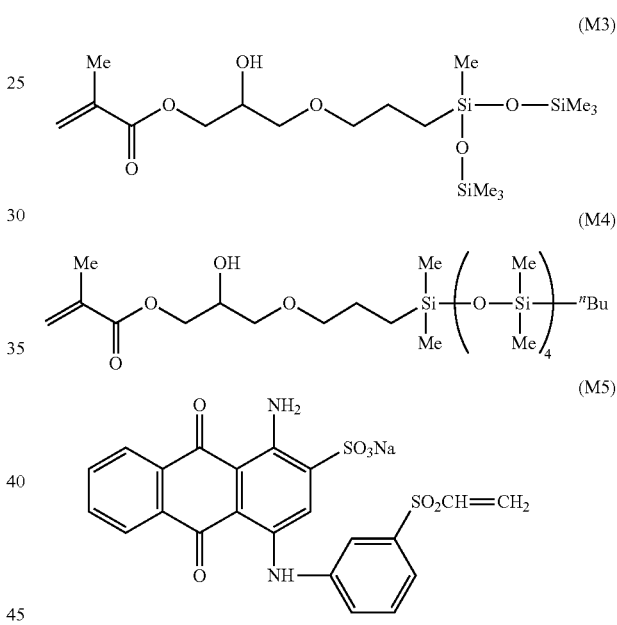

Reference Example 7

Mixed were polydimethylsiloxane having methacryloyl groups at both ends (FM7726, JNC, the compound of Formula (M2), mass average molecular weight 29 kD, number average molecular weight 26 kD) (40 parts by mass) as the component A, trifluoroethyl acrylate (Viscoat 3F, Osaka Organic Chemical Industry Ltd.) (45 parts by mass) as the component B, 2-ethylhexyl acrylate (3 parts by mass) as the component C, dimethylaminoethyl acrylate (1 part by mass) as the component C, an ultraviolet absorber having a polymerizable group (RUVA-93, Otsuka Chemical Co., Ltd.) (1 part by mass) as the component C, the acid type Uniblue A of Reference Example 1 (0.04 parts by mass) as the component C, a polymerization initiator "Irgacure (registered trademark)" 819 (Ciba Specialty Chemicals, 0.75 parts by mass), t-amyl alcohol (10 parts by mass), and polydimethylsiloxane having a methacryloyl group at its one end (FM0721, JNC, the compound of Formula (M6), mass average molecular weight 6.8 kD, number average molecular weight 6.5 kD) (10 parts by mass) as the component M. The mixture was stirred and filtered with a membrane filter (0.45 μm) to remove insolubles and obtain a monomer mixture. This monomer mixture was put into a test tube, which was deaerated with its pressure reduced to 20 Torr (27 hPa) while it was stirred by a touch mixer and then returned to the atmospheric pressure with argon gas. This operation was repeated three times. Within a glove box in a nitrogen atmosphere, the monomer mixture was injected into a contact lens mold formed of transparent resin (propylene on the base curve side and Zeonor on the front curve side) and was irradiated with light (1.01 mW/cm$^2$, for 20 minutes) using a fluorescent lamp (Toshiba, FL-6D, daylight, 6 W, a set of four) to be polymerized. After being polymerized and immersed into a 60%-by-mass isopropyl alcohol aqueous solution together with the mold, a contact lens-shaped molded body was peeled off from the mold. The thus obtained molded body was immersed into a largely excessive amount of 80%-by-mass isopropyl alcohol aqueous solution at 60° C. for two hours. The molded body was further immersed into a largely excessive amount of 50%-by-mass isopropyl alcohol aqueous solution at room temperature (23° C.) for 30 minutes, immersed into a largely excessive amount of 25%-by-mass isopropyl alcohol aqueous solution at room temperature (same as above) for 30 minutes, and immersed into a largely excessive amount of pure water at room temperature (same as above) for two hours or more. The diameter of the perimeter of the obtained lens was about 14 mm, and the thickness at the center thereof was about 0.07 mm.

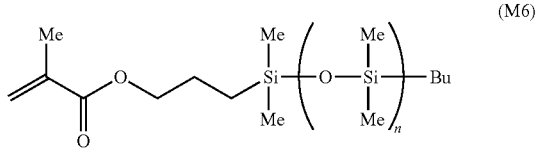

(M6)

Example 1

The molded body obtained in Reference Example 3 was immersed into the PAA solution at room temperature (25° C.) for 30 minutes and then lightly rinsed with pure water in a beaker. The molded body was transferred to another beaker containing fresh pure water, and the beaker was put through an ultrasonic cleaner (30 seconds). The molded body was further lightly rinsed in another beaker containing fresh pure water. Subsequently, the same operations were repeated with the PEI solution and the p(DMAA/AA) solution in this order. After the completion of the coating operation, the coated molded body was immersed into a borate buffer solution in a sealed vial, and gamma rays were applied thereto. The gamma dose was 35 kGy. The evaluation results are listed in Table 1.

Example 2

The molded body obtained in Reference Example 3 was immersed into the PAA solution at room temperature (25° C.) for 30 minutes and then lightly rinsed with pure water in a beaker. The molded body was transferred to another beaker containing fresh pure water, and the beaker was put through an ultrasonic cleaner (30 seconds). The molded body was further lightly rinsed in another beaker containing fresh pure water. Subsequently, the same operations were repeated with the PEI solution and the PAA solution in this order. After the completion of the coating operation, the coated molded body was immersed into a borate buffer solution in a sealed vial, and gamma rays were applied thereto. The gamma dose was 35 kGy. The evaluation results are listed in Table 1.

Example 3

The molded body obtained in Reference Example 4 was immersed into the PAA solution at room temperature (25° C.) for 30 minutes and then lightly rinsed with pure water in a beaker. The molded body was transferred to another beaker containing fresh pure water, and the beaker was put through an ultrasonic cleaner (30 seconds). The molded body was further lightly rinsed in another beaker containing fresh pure water. Subsequently, the same operations were repeated with the PEI solution and the p(DMAA/AA) solution in this order. After the completion of the coating operation, the coated molded body was immersed into a borate buffer solution in a sealed vial, and gamma rays were applied thereto. The gamma dose was 35 kGy. The evaluation results are listed in Table 1.

Example 4

The molded body obtained in Reference Example 4 was immersed into the PAA solution at room temperature (25° C.) for 30 minutes and then lightly rinsed with pure water in a beaker. The molded body was transferred to another beaker containing fresh pure water, and the beaker was put through an ultrasonic cleaner (30 seconds). The molded body was further lightly rinsed in another beaker containing fresh pure water. Subsequently, the same operations were repeated with the PEI solution and the PAA solution in this order. After the completion of the coating operation, the coated molded body was immersed into a borate buffer solution in a sealed vial, and gamma rays were applied thereto. The gamma dose was 35 kGy. The evaluation results are listed in Table 1.

TABLE 1

| | Base material subjected to coating | First solution | Second solution | Third solution | Gamma-ray irradiation | Gamma-ray irradiation solution | Evaluation results | | | | |
|---|---|---|---|---|---|---|---|---|---|---|---|
| | | | | | | | Si atom content (% by mass) | Water content (% by mass) | Wettability | Slidability | Resistance to rubbing for cleaning |
| Example 1 | Reference Example 3 | PAA solution | PEI solution | p(DMAA/AA) solution | Irradiated | Borate buffer solution | 19 | Less than 1 | C | A | A |
| Example 2 | Reference Example 3 | PAA solution | PEI solution | PAA solution | Irradiated | Borate buffer solution | 19 | Less than 1 | C | B | B |
| Example 3 | Reference Example 4 | PAA solution | PEI solution | p(DMAA/AA) solution | Irradiated | Borate buffer solution | 19 | Less than 1 | C | A | A |

TABLE 1-continued

| | Base material subjected to coating | First solution | Second solution | Third solution | Gamma-ray irradiation | Gamma-ray irradiation solution | Si atom content (% by mass) | Water content (% by mass) | Wettability | Slidability | Resistance to rubbing for cleaning |
|---|---|---|---|---|---|---|---|---|---|---|---|
| Example 4 | Reference Example 4 | PAA solution | PEI solution | PAA solution | Irradiated | Borate buffer solution | 19 | Less than 1 | C | B | B |
| Comparative Example 1 | Reference Example 3 | PAA solution | PEI solution | p(DMAA/AA) solution | Not irradiated | — | 19 | Less than 1 | C | A | C |
| Comparative Example 2 | Reference Example 3 | PAA solution | PEI solution | p(DMAA/AA) solution | Only base material irradiated | Borate buffer solution | 19 | Less than 1 | C | C | D |
| Comparative Example 3 | Reference Example 5 | — | — | — | Not irradiated | — | 0 | 37 | D | D | D |
| Comparative Example 4 | O2 OPTIX | — | — | — | Not irradiated | — | N/A | 18.6 | D | D | D |
| Comparative Example 5 | Reference Example 6 | — | — | — | irradiated | Alkox L-6 | 11.1 | 35 | Unmeasurable due to polymer adhesion to lens surface | | |
| Comparative Example 6 | Reference Example 6 | — | — | — | Irradiated | Alkox L-11 | 11.1 | 35 | Unmeasurable due to polymer adhesion to lens surface | | |
| Comparative Example 7 | Reference Example 6 | — | — | — | Irradiated | Alkox EP-20 | 11.1 | 35 | Unmeasurable due to polymer adhesion to lens surface | | |

Comparative Example 1

The molded body obtained in Reference Example 3 was immersed into the PAA solution at room temperature (25° C.) for 30 minutes and then lightly rinsed with pure water in a beaker. The molded body was transferred to another beaker containing fresh pure water, and the beaker was put through an ultrasonic cleaner (30 seconds). The molded body was further lightly rinsed in another beaker containing fresh pure water. Subsequently, the same operations were repeated with the PEI solution and the p(DMAA/AA) solution in this order. After the completion of the coating operation, the coated molded body was immersed into a borate buffer solution in a sealed vial and subjected to autoclave sterilization at 121° C. for 30 minutes. The evaluation results are listed in Table 1.

Comparative Example 2

The molded body obtained in Reference Example 3 was immersed into a borate buffer solution in a sealed vial, and gamma rays were applied thereto. The gamma dose was 35 kGy. The molded body after irradiated with gamma rays was lightly rinsed with pure water in a beaker. The molded body was then immersed into the PAA solution at room temperature (25° C.) for 30 minutes and then lightly rinsed with pure water in a beaker. The molded body was transferred to another beaker containing fresh pure water, and the beaker was put through an ultrasonic cleaner (30 seconds). The molded body was further lightly rinsed in another beaker containing fresh pure water. Subsequently, the same operations were repeated with the PEI solution and the p(DMAA/AA) solution in this order. After the completion of the coating operation, the coated molded body was immersed into a borate buffer solution in a sealed vial and subjected to autoclave sterilization at 121° C. for 30 minutes. The evaluation results are listed in Table 1.

Comparative Example 3

The molded body obtained in Reference Example 4 was immersed into a borate buffer solution in a sealed vial and subjected to autoclave sterilization at 121° C. for 30 minutes. The evaluation results are listed in Table 1.

Comparative Example 4

A commercial contact lens "O$_2$ OPTIX (registered trademark) (manufactured by Ciba Vision K.K.) was lightly rinsed with pure water in a beaker. It was then transferred to another beaker containing fresh pure water, and the beaker was put through an ultrasonic cleaner (30 seconds). It was further lightly rinsed in another beaker containing fresh pure water. The evaluation results are listed in Table 1.

Comparative Example 5

The molded body obtained in Reference Example 5 was immersed into a 0.8%-by-mass aqueous solution of Alkox L-6 (ethylene oxide, Mw 60,000, manufactured by Meisei Chemical Works, Ltd.) and subjected to autoclave sterilization at 121° C. for 30 minutes. The evaluation results are listed in Table 1.

Comparative Example 6

The molded body obtained in Reference Example 5 was immersed into a 0.8%-by-mass aqueous solution of Alkox L-11 (ethylene oxide, Mw 110,000, manufactured by Meisei Chemical Works, Ltd.) and subjected to autoclave sterilization at 121° C. for 30 minutes. The evaluation results are listed in Table 1.

Comparative Example 7

The molded body Obtained in Reference Example 5 was immersed into a 0.8%-by-mass aqueous solution of Alkox EP-20 (copolymer, ethylene oxide/propylene oxide=80/20 (in percent-by-mass ratio), Mw 800,000, manufactured by Meisei Chemical Works, Ltd.) and subjected to autoclave sterilization at 121° C. for 30 minutes. The evaluation results are listed in Table 1.

Example 5

The molded body obtained in Reference Example 7 was immersed into the PAA solution at room temperature (23° C.) for 30 minutes and then lightly rinsed with pure water in a beaker. The molded body was transferred to another beaker containing fresh pure water, and the beaker was put through an ultrasonic cleaner (30 seconds). The molded body was further lightly rinsed in another beaker containing fresh pure water. Subsequently, the same operations were repeated with the PEI solution and the p(DMAA/AA) solution in this order. After the completion of the coating operation, the coated molded body was put into a sealed vial, and gamma rays of 25 kGy were applied thereto. Evaluated on this molded body were the amount of coating, a water content, a contact angle, wettability, and slidability. The evaluation results are listed in Table 2.

The symbol X in Table 2 represents the N/Si element content ratio on a lens surface before coating, the symbol Y represents the N/Si element content ratio on the lens surface before rubbing a product after coating for cleaning, and the symbol Z represents the N/Si element content ratio on the lens surface after rubbing the product after coating for cleaning.

Example 6

The molded body obtained in Reference Example 7 was immersed into the PAA solution at room temperature (23° C.) for 30 minutes and then lightly rinsed with pure water in a beaker. The molded body was transferred to another beaker containing fresh pure water, and the beaker was put through an ultrasonic cleaner (30 seconds). The molded body was further lightly rinsed in another beaker containing fresh pure water. Subsequently, the same operations were repeated with the PEI solution and the p(DMAA/AA) solution in this order. After the completion of the coating operation, the coated molded body was put into a sealed vial, and gamma rays of 10 kGy were applied thereto.

After irradiated with gamma rays, the molded body was placed in a recess formed on a palm, and both sides thereof were rubbed 100 times each with the ball of the forefinger of the other hand while flowing water. Evaluated on this molded body were the amount of coating, a water content, a contact angle, wettability, and slidability. The evaluation results are listed in Table 2.

Example 7

The molded body obtained in Example 5 was placed in a recess formed on a palm, and both sides thereof were rubbed 100 times each with the ball of the forefinger of the other hand while flowing water. Evaluated on this molded body were the amount of coating, a water content, a contact angle, wettability, and slidability. The evaluation results are listed in Table 2.

Example 8

A molded body was formed in the same manner as Example 5 except that the radiation to be applied to the molded body after coating was gamma rays of 1 kGy. Rubbing for cleaning treatment was performed on the molded body in the same manner as Example 7, and the amount of coating was evaluated. The evaluation results are listed in Table 2.

Example 9

A molded body was formed in the same manner as Example 5 except that the radiation to be applied to the molded body after coating was electron rays of 1 kGy. Rubbing for cleaning treatment was performed on the molded body in the same manner as Example 7, and the amount of coating was evaluated. The evaluation results are listed in Table 2.

Example 10

A molded body was formed in the same manner as Example 5 except that the radiation to be applied to the molded body after coating was electron rays of 10 kGy. Rubbing for cleaning treatment was performed on the molded body in the same manner as Example 7, and the amount of coating was evaluated. The evaluation results are listed in Table 2.

Example 11

A molded body was formed in the same manner as Example 5 except that the radiation to be applied to the molded body after coating was electron rays of 40 kGy. Rubbing for cleaning treatment was performed on the molded body in the same manner as Example 7, and the amount of coating was evaluated. The evaluation results are listed in Table 2.

Comparative Example 8

A molded body was formed in the same manner as Example 5 except that the radiation to be applied to the molded body after coating was gamma rays of 0.3 kGy. Rubbing for cleaning treatment was performed on the molded body in the same manner as Example 7, and the amount of coating was evaluated. The evaluation results are listed in Table 2.

Comparative Example 9

A molded body was formed in the same manner as Example 5 except that the radiation to be applied to the molded body after coating was gamma rays of 40 kGy. Rubbing for cleaning treatment was performed on the molded body in the same manner as Example 7, and the amount of coating was evaluated. The evaluation results are listed in Table 2.

Comparative Example 10

A molded body was formed in the same manner as Example 5 except that the radiation to be applied to the molded body after coating was gamma rays of 50 kGy. Rubbing for cleaning treatment was performed on the molded body in the same manner as Example 7. Evaluated were the amount of coating, a water content, a contact angle, wettability, and slidability. The evaluation results are listed in Table 2.

Comparative Example 11

The molded body obtained in Reference Example 7 was immersed into the PAA solution at room temperature (23° C.) for 30 minutes and then lightly rinsed with pure water in a beaker. The molded body was transferred to another beaker containing fresh pure water, and the beaker was put through an ultrasonic cleaner (30 seconds). The molded body was further lightly rinsed in another beaker containing fresh pure water. Subsequently, the same operations were repeated with the PEI solution and the p(DMAA/AA) solution in this order. After that, rubbing for cleaning treatment was performed in the same manner as Example 7. Evaluated were the amount of coating, a water content, a contact angle, wettability, and slidability. The evaluation results are listed in Table 2.

Comparative Example 12

Evaluated on the molded body obtained in Reference Example 7 were the amount of coating, a water content, a contact angle, wettability, and slidability. The evaluation results are listed in Table 2.

TABLE 2

| | Coating | Radiation | Dose | Rubbing for cleaning | N/Si | X | Y | Z | Y − X | Z − X | Y − Z | Water content (% by mass) | Contact angle (°) | Wettability | Slidability |
|---|---|---|---|---|---|---|---|---|---|---|---|---|---|---|---|
| Example 5 | Present | Gamma rays | 25 kGy | Absent | 0.091(Y) | 0.009 | 0.091 | — | 0.08 | — | — | Less than 1 | 30.5 | C | A |
| Example 6 | Present | Gamma rays | 10 kGy | Present | 0.077(Z) | 0.009 | 0.091 | 0.077 | 0.08 | 0.06 | 0.01 | Less than 1 | 35.0 | C | A |
| Example 7 | Present | Gamma rays | 25 kGy | Present | 0.058(Z) | 0.009 | 0.091 | 0.058 | 0.08 | 0.05 | 0.03 | Less than 1 | 38.0 | C | A |
| Example 8 | Present | Gamma rays | 1 kGy | Present | 0.061(Z) | 0.009 | 0.091 | 0.061 | 0.08 | 0.05 | 0.03 | — | — | — | — |
| Example 9 | Present | Electron rays | 1 kGy | Present | 0.056(Z) | 0.009 | 0.091 | 0.056 | 0.08 | 0.05 | 0.04 | — | — | — | — |
| Example 10 | Present | Electron rays | 10 kGy | Present | 0.044(Z) | 0.009 | 0.091 | 0.044 | 0.08 | 0.04 | 0.05 | — | — | — | — |
| Example 11 | Present | Electron rays | 40 kGy | Present | 0.055(Z) | 0.009 | 0.091 | 0.055 | 0.08 | 0.05 | 0.04 | — | — | — | — |
| Comparative Example 8 | Present | Gamma rays | 0.3 kGy | Present | 0.031(Z) | 0.009 | 0.091 | 0.031 | 0.08 | 0.02 | 0.06 | — | — | — | — |
| Comparative Example 9 | Present | Gamma rays | 40 kGy | Present | 0.031(Z) | 0.009 | 0.091 | 0.031 | 0.08 | 0.02 | 0.06 | — | — | — | — |
| Comparative Example 10 | Present | Gamma rays | 50 kGy | Present | 0.029(Z) | 0.009 | 0.091 | 0.029 | 0.08 | 0.02 | 0.06 | Less than 1 | 51.0 | C | C |
| Comparative Example 11 | Present | Not irradiated | | Present | 0.032(Z) | 0.009 | 0.091 | 0.032 | 0.08 | 0.02 | 0.06 | Less than 1 | 90.0 | C | C |
| Comparative Example 12 | Absent | Not irradiated | | Absent | 0.009(X) | 0.009 | — | — | — | — | — | Less than 1 | 105.0 | D | D |

REFERENCE SIGNS LIST

1 Synthetic leather
2 Sample film
3 Rubber plate
4 Plastic container containing an iron ball

The invention claimed is:

1. A low hydrous soft ophthalmic lens comprising:
a base material; and
a layer formed of a hydrophilic polymer on at least part of a surface of the base material, at least part of inside of the layer being cross-linked,
wherein the low hydrous soft ophthalmic lens has a water content of less than 1% by mass.

2. The low hydrous soft ophthalmic lens according to claim 1, wherein the hydrophilic polymer is an acidic polymer and/or basic polymer.

3. The low hydrous soft ophthalmic lens according to claim 1, wherein the base material and the layer cross-link therebetween at least partially.

4. The low hydrous soft ophthalmic lens according to claim 1, wherein part of the inside of the layer is cross-linked by irradiating the base material with radiation while the hydrophilic polymer is attached to the base material.

5. The low hydrous soft ophthalmic lens according to claim 1, wherein the base material has, as a main component, a polymer of a component A below or a copolymer of the component A below and a component B below:
the component A is a polysiloxane compound having a plurality of polymerizable functional groups per molecule and a number average molecular weight of 6,000 or more; and
the component B is a polymerizable monomer having a fluoroalkyl group.

6. The low hydrous soft ophthalmic lens according to claim 1, wherein the layer is formed by performing treatment with an acidic polymer solution once or twice and treatment with a basic polymer solution once or twice, these pieces of treatment being performed three times in total.

7. The low hydrous soft ophthalmic lens according to claim 6, wherein the layer is formed by performing treatment with two kinds of acidic polymer solutions twice and treatment with a basic polymer solution once.

8. The low hydrous soft ophthalmic lens according to claim 1, wherein at least one kind of hydrophilic polymer forming the layer is a polymer having a group selected from a hydroxy group and an amido group.

* * * * *